US010028906B2

(12) United States Patent
Riser

(10) Patent No.: US 10,028,906 B2
(45) Date of Patent: Jul. 24, 2018

(54) METHOD AND KIT FOR TREATING A SOLID TUMOR AND ASSOCIATED DESMOPLASIA

(71) Applicant: Rosalind Franklin Univ. of Medicine and Science, North Chicago, IL (US)

(72) Inventor: Bruce L. Riser, Kenosha, WI (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 15/466,436

(22) Filed: Mar. 22, 2017

(65) Prior Publication Data

US 2017/0281574 A1    Oct. 5, 2017

Related U.S. Application Data

(60) Provisional application No. 62/311,692, filed on Mar. 22, 2016.

(51) Int. Cl.
| | |
|---|---|
| *A61K 38/10* | (2006.01) |
| *A61K 9/00* | (2006.01) |
| *A61K 45/06* | (2006.01) |
| *A61K 31/4745* | (2006.01) |
| *A61K 31/513* | (2006.01) |
| *A61K 31/519* | (2006.01) |
| *A61K 31/555* | (2006.01) |
| *A61K 31/7068* | (2006.01) |
| *A61K 33/24* | (2006.01) |

(52) U.S. Cl.
CPC .......... *A61K 9/0031* (2013.01); *A61K 9/0014* (2013.01); *A61K 9/0019* (2013.01); *A61K 31/4745* (2013.01); *A61K 31/513* (2013.01); *A61K 31/519* (2013.01); *A61K 31/555* (2013.01); *A61K 31/7068* (2013.01); *A61K 33/24* (2013.01); *A61K 45/06* (2013.01); *A61K 9/0012* (2013.01)

(58) Field of Classification Search
None
See application file for complete search history.

(56) References Cited

U.S. PATENT DOCUMENTS

| | | |
|---|---|---|
| 7,780,949 B2 | 8/2010 | Riser |
| 8,518,395 B2 | 8/2013 | Riser |
| 9,114,112 B2 | 8/2015 | Riser |
| 2003/0059768 A1 | 3/2003 | Vernet et al. |
| 2004/0009940 A1 | 1/2004 | Coleman et al. |
| 2004/0191230 A1 | 9/2004 | Auclair et al. |
| 2004/0224360 A1 | 11/2004 | Riser et al. |
| 2006/0004101 A1 | 1/2006 | Okita et al. |
| 2006/0178332 A1 | 8/2006 | Riser |
| 2007/0059314 A1 | 3/2007 | Plouet et al. |
| 2010/0004169 A1 | 1/2010 | Irvine et al. |
| 2011/0250180 A1* | 10/2011 | Riser ............... A61K 38/08 424/93.7 |

FOREIGN PATENT DOCUMENTS

| | | |
|---|---|---|
| EP | 1382347 A1 | 1/2004 |
| WO | 2004/090109 A2 | 10/2004 |
| WO | 2006/036962 A2 | 4/2006 |
| WO | 2006/074452 A2 | 7/2006 |

OTHER PUBLICATIONS

Rachfal et al., Journal of Clinical Pathology (2004) 57, 422-425).*
Whatcott et al., "Desmoplasia and Chemoresistance in Pancreatic Cancer" in: Grippo PJ, Munshi HG, editors. Pancreatic Cancer and Tumor Microenvironment. Trivandrum (India): Transworld Research Network; 2012. Chapter 8. Available from: https://www.ncbi.nlm.nih.gov/books/NBK98939/, accessed on Sep. 1, 2017.*
Vetelainen et al., "Steatosis as a Risk Factor in Liver Surgery," Annals of Surgery, vol. 245, No. 1, Jan. 2007.
Akchurn et al., "Update on Inflammation in Chronic Kidney Disease," Blood Purification 2015; 39:84-92, Published online: Jan. 20, 2015.
Bataller et al., "Liver fibrosis," Science in Medicine, The Journal of Clinical Investigation, vol. 115, No. 2, Feb. 2005.
Leask et al., "Connective tissue growth factor (CTGF, CCN2) gene regulation: a potent clinical bio-marker of fibroproliferative disease?", J. Cell Commun. Signal, 3:89-94, Published online Jan. 21, 2009.
Dongiovanni et al., "Genetic Predisposition in NAFLD and NASH: Impact on Severity of Liver Disease and Response to Treatment," Current Pharmaceutical Design, 19, 5219-5238, 2013.
Canadian Liver Foundation, Issues in Liver Health, Livewell, URL: <http://www.liver.ca/livewell/issues/2010_issue_spring_issues_liver_cancer.aspx>, Spring 2010.
Gressner et al., "Connective tissue grown factor: a fibrogenic master switch in fibrotic liver diseases," Liver International, ISSN 1478-3223, 2008.
Wang et al., "Adverse effects of high glucose and free fatty acid on cardiomyocytes are mediated by connective tissue growth factor," Am J Physiol Cell Physiol 297, C1490-C1500, First published Jul. 22, 2009.

(Continued)

*Primary Examiner* — Satyanarayana R Gudibande
(74) *Attorney, Agent, or Firm* — Joseph A. Fuchs; Greensfelder, Hemker & Gale, P.C.

(57) ABSTRACT

A kit for treating a human patient with a solid tumor with a desmoplasia associated therewith having: (1) a container of and effective amount of a CCNp37 (SEQ ID No. 37), CCNp38 (SEQ ID No. 38) or a combination of CCNp37 and CCNp38 (SEQ ID Nos. 37 and 38); (2) a container of an effective amount of a chemotherapeutic agent or an immunotherapeutic agent; and (3) instructions for administering these components which can involve a pretreatment with the CCNp37 (SEQ ID No. 37), CCNp38 (SEQ ID No. 38) or a combination of CCNp37 and CCNp38 (SEQ ID Nos. 37 and 38) to a patient in need thereof.

18 Claims, 17 Drawing Sheets

(56) References Cited

OTHER PUBLICATIONS

Daniels et al., "Connective tissue growth factor and cardiac fibrosis," Acta Physiologica, 2009, 195, 321-338, Journal Complication 2008.
Schellenberger et al., "A recombinant polypeptide extends the in vivo half-life of peptides and proteins in a tunable matter," Nature Biotechnology, vol. 27, No. 12, Dec. 2009.
Liu et al., "Nephroblastoma overexpressed gene (NOV) codes for a growth factor that induces protein tyrosine phosphorylation," Gene an International Journal on Genes and Genomes, Gene 238 (1999), 471-478, 1999.
Le Guillou, "Vaccines Information," URL: <https://www.alainleguillou.com/medical-information>, downloaded on Jan. 1, 2014.
Leslie, "Tumor Blocker May Fight Fibrosis," Science/AAAS, News, URL: <http://news.sciencemag.org/health/2012/05/tumor-blocker-may-tight-fibrosis>, Published online May 30, 2012.
Panos et al., "Clinical deterioration in patients with idiopathic pulmonary fibrosis: causes and assessment," Am J Med. Apr. 1990, 88(4) 396-404, URL: <http:www.ncbi.nlm.nih.gov/pubmed/2183601>, downloaded on Oct. 22, 2013.
Brigstock, "Regulation of angiogenesis and endothelial cell function by connective tissue growth factor (CTGF) and cysteine-rich 61 (CYR61)," Angiogenesis 5: 153-165, 2002; Copyrighted 2003.
Mason, "Connective tissue growth factor(CCN2), a pathogenic factor in diabetic nephropathy. What does it do? How loes it do it?", J. Cell Commun. Signal (2009), 3:95-104, Published online Feb. 14, 2009.
Riser et al., "CCN3 (NOV) Is a Negative Regulator of CCN2 (CTGF) and a Novel Endogenous Inhibitor of the Fibrotic Pathway in an in Vitro Model of Renal Disease," The American Journal of Pathology, vol. 174, No. 5, May 2009.
McCallum et al., "CCN3: a key growth regulator in Chronic Myeloid Leukaemia," J. Cell Commun. Signal (2009) 3:115-124, Published online Jul. 22, 2009.
Riser et al., "Gadolinium-induced fibrosis is counter-regulated by CCN3 in human dermal fibroblasts: a model for potential treatment of nephrogenic systemic fibrosis," J. Cell, Commun. Signal, Published online May 31, 2012.
Brigstock, "Connective tissue grown factor (CCN2, CTGF) and organ fibrosis: lessons from transgenic animals," J. Cell Commun. Signal (2010) 4:1-4, Published online Oct. 2, 2009.
Bhagavathula et al., "Fibroblast Response to Gadolinium: Role for Platelet-Derived Growth Factor Receptor," Invest Radiol, 45(12), 769-77, Dec. 2010.
Kular et al., "NOV/CCN3 attenuates inflammatory pain through regulation of matrix metalloproteinases-2 and -9," Journal of Neuroinflammation, 9:36, Copyrighted 2012.
Ghosh et al., "PAI-1 in Tissure Fibrosis," Journal of Cellular Physiology, pp. 493-507, Published online in Wiley Online Library (wileyonlinelibrary.com), Apr. 4, 2011.
McIntosh et al., "Selective CCR2-targeted macrophage depletion ameliorates experimental mesangioproliferative glomerulonephritis," Clinical & Experimental Immunology, The Journal of Translational Immunology, 155: 295-303, Accepted for publication Oct. 9, 2008.
Tsoutsman et al., "Severe Heart Failure and Early Mortality in a Double-Mutation Mouse Model of Familial Hypertrophic Cardiomyopathy," pp. 1820-1831, Apr. 8, 2008.
Cozzolino et al., "CCN2 (CTGF) Gene Polymorphism Is a Novel Prognostic Risk Factor for Cardiovascular Outcomes in Hemodialysis Patients," Blood Purif 2010;30:272-276, www.karger.com/bpu, Published online Nov. 11, 2010.
Perbal, "NOV (nephroblastoma overexpressed) and the CCN family of genes: structural and functional issues," J. Clin. Pathol: Mol. Pathol., 54:57-79, 2001.
Sampath et al., Aberrant Expression of Cyr61, a Member of the CCN (CTGF/Cyr61/Cef10/NOVH) Family, and Dysregulation by 17 beta-Estradiol and Basic Fibroblast Growth Factor in Human Uterine Leiomyomas, The Journal of Clinical Endocrinology and Metabolish, vol. 86, No. 4, Downloaded from jcem.endojournals.org on Jul. 6, 2007.
Sampath et al., "The Angiogenic Factor Cyr61 Is Induced by the Progestin R5020 and Is Necessary for Mammary Adenocarcinoma Cell Growth," Endocrine, vol. 18, No. 2, 147-159, Humana Press Inc., Jul. 2002.
Xie et al., "Breast Cancer, Cyr61 Is Overexpressed, Estrogen-Inducible, and Associated With More Advanced Disease," The Journal of Biological Chemistry, vol. 276, No. 17, pp. 14187-14194, Issue of Apr. 27, 2001.
Bradham et al., "Connective Tissue Growth Factor: a Cysteine-rich Mitogen Secreted by Human Vascular Endothelial Cells Is Related to the SRC-induced Immediate Early Gene Product CEF-10," The Journal of Cell Biology, vol. 114, No. 6, pp. 1285-1294, Sep. 1991.
Tsai et al., Expression and Function of CYR61, an Angiogenic Factor, in Breast Cancer Cell Lines and Tumor Biopsies, Cancer Research 60, pp. 5603-5607, Oct. 15, 2000.
Cheon et al., "A Genomic Approach to Identify Novel Progesterone Receptor Regulated Pathways in the Uterus during Implantation," Molecular Endocrinology, 16(12); pp. 2853-2871; 2002.
Rageh et al., "Steroidal regulation of connective tissue growth factor (CCN2; CTGF) synthesis in the mouse uterus," J. Clin. Pathol: Mol. Pathol., 54: pp. 338-346, 2001.
Wandji et al., "Messenger Ribonucleic Acids for MAC25 and Connective Tissue Growth Factor (CTGF) Are Inversely Regulated during Folliculogenesis and Early Luteogenesis," Endocrinology, vol. 141, No. 7, pp. 2648-2657, 2000.
Slee et al., "Differentiation-Dependent Expression of Connective Tissue Growth Factor and Lysyl Oxidase Messenger Ribonucleic Acids in Rat Granulosa Cells," Endocrinology, vol. 142, No. 3, pp. 1082-1089, 2001.
Harlow et al., "Connective tissue growth factor in the ovarian paracrine system," Molecular and Cellular Endocrinology, 187, pp. 23-27, 2002.
Harlow et al., "FSH and TGF-beta Superfamily Members Regulate Granulosa Cell Connective Tissue Growth Factor Gene Expression in Vitro and in Vivo," Endocrinology, 143(9), pp. 3316-3325, 2002.
Zarrinkalam et al., "Connective tissue growth factor and its regulation in the peritoneal cavity of peritoneal dialysis patients," Kidney International, vol. 64, pp. 331-338, 2003.
Riser et al., "Urinary CCN2 (CTGF) as a possible predictor of diabetic nephropathy: Preliminary report," Kidney International, vol. 64, pp. 451-458, 2003.
Wang et al., "Connective tissue growth factor in tubulointerstitial injury of diabetic nephropathy," Kidney International, vol. 60, pp. 96-105, 2001.
Perbal, "CCN3: Doctor Jekyll and Mister Hyde," J. Cell Commun. Signal, 2: 3-7, 2008.
Yeger et al., "The CCN family of genes: a perspective on CCN biology and therapeutic potential," J. Cell Commun. Signal, 1: 159-164, 2007.
Brigstock, "The CCN family: a new stimulus package," Journal of Endocrinology, 178, pp. 169-175, 2003.
Jaeger et al., "Cerebral Ischemia Detected with Diffusion-Weighted MR Imaging after Stent Implantation in teh Carotid Artery," AJNR Am. J. Neuroradiol, 23: 200-207, Feb. 2002.
Gupta et al. "NOV (CCN3) Functions as a Regulator of Human Hematopoietic Stem or Progenitor Cells," Science, vol. 316, Abstract and pp. 590-593, 2007.
Tsai et al., "Expression and regulation of Cyr61 in human breast cancer cell lines," Oncogene, 21, pp. 964-973, 2002.
Perbal, "The CCN3 (NOV) cell growth regulator: a new tool for molecular medicine," Expert Rev. Mol. Diagn., 3(5): 597-604, Abstract, Sep. 2003.
Sampath et al., "Cyr61, a Member of teh CCN Family, Is Required for MCF-7 Cell Proliferation: Regulation by 17 beta-Estradiol and Overexpression in Human Breast Cancer," Endocrinology, vol. 142, No. 6, pp. 2540-2548, Downloaded from endo.endojournals.org on Jul. 6, 2007.

(56) References Cited

OTHER PUBLICATIONS

Xie et al., Elevated Levels of Connective Tissue Growth Factor, WISP-1, and CYR61 in Primary Breast Cancers Associated with More Advanced Features, Cancer Research, 61, pp. 8917-8923, Dec. 15, 2001.

Liu et al., "Gonadotrophins inhibit the expression of insulin-like growth factor binding protein-related protein-2 mRNA in cultured human granulosa-luteal cells," Molecular Human Reproduction, vol. 8, No. 2, pp. 136-141, 2002.

Kyurkchiev, et al., "Potential cellular conformations of the CCN3(NOV) protein," Cell Communication and Signaling, 2:9, pp. 1-9, Sep. 10, 2004.

Li et al., "A role for CCN3 (NOV) in calcium signalling," Journal of Clinical Pathology: Molecular Pathology, 55, pp. 250-261, May 14, 2002.

Dean et al., "Connective Tissue Growth Factor and Cardiac Fibrosis after Myocardial Infarction," Journal of Histochemistry and Cytochemistry, vol. 53(10), pp. 1245-1256, 2005.

Shi-Wen et al., "Autocrine Overexpression of CTGF Maintains Fibrosis: RDA Analysis of Fibrosis Genes in Systemic Sclerosis," Experimental Cell Research, 259, pp. 213-224, 2000.

Ozaki et al., "Diffuse expression of heparan sulfate proteoglycan and connective tissue growth factor in fibrous septa with many mast cells relate to unresolving hepatic fibrosis of congenital hepatic fibrosis," Liver International, 25, pp. 817-828, 2005.

Sakamoto et al., "Influence of glucose and inflammatory cytokines on TGF-beta1 and CTGF mRNA expressions in human peritoneal mesothelial cells," International Journal of Molecular Medicine, 15, pp. 907-911, 2005.

Uniprot-Direct Submission P48745 (Mar. 2, 2010), Retrieved from Internet Jul. 7, 2011, ,http://www.uniprot.org/uniprot/P487 4 5. txt?version-94>>.

* cited by examiner

*IN VITRO* EXPERIMENTS
MIA PaCa2-Luc - EFFECT ON CANCER CELL GROWTH OF PEPTIDE ALONE OR IN COMBINATION WITH GEMCITIBINE (GEM)

*IN VITRO* EXPERIMENTS

NEITHER PEPTIDE HAD AN EFFECT ON PROLIFERATION OF CANCER FC1199
STIMULUS: FCS 1% (SIMILAR DATA USING PDGF OR FCS 5%)
MEAN OF VALUES FROM 2 DIFFERENT EXPERIMENTS

IN VIVO EXPERIMENTS

RESPONSE OF FC1199 TUMORS TO GEMCITABINE
(20-40-80 mg/kg i.p., 2 TIMES PER WEEK)

GEMCITABINE PRODUCES A DOSE-DEPENDENT REDUCTION IN TUMOR
BURDEN IN FC1199 TUMORS

TOXICITY

*IN VIVO* EXPERIMENTS
RESPONSE OF FC1199 TUMORS TO PEPTIDE 2
*INTERIM ANALYSIS (DAY 13)*

*IN VIVO* EXPERIMENTS
RESPONSE OF FC1199 TUMORS TO PEPTIDE 2 + GEMCITABINE
*FINAL ANALYSIS (DAY 24)*

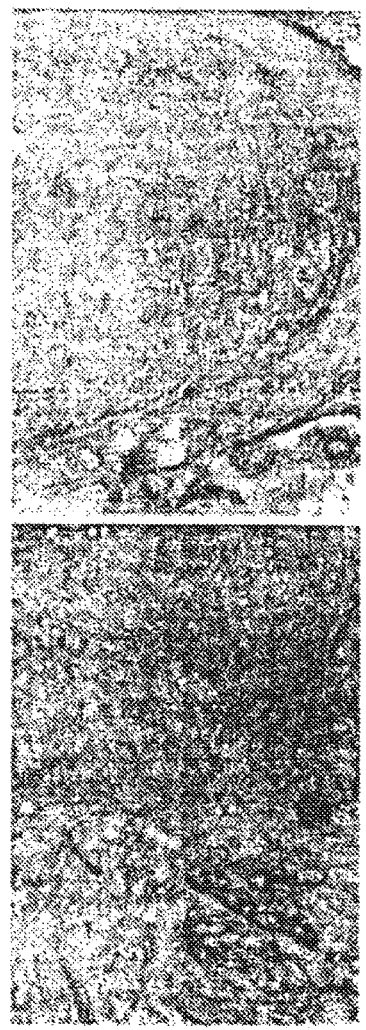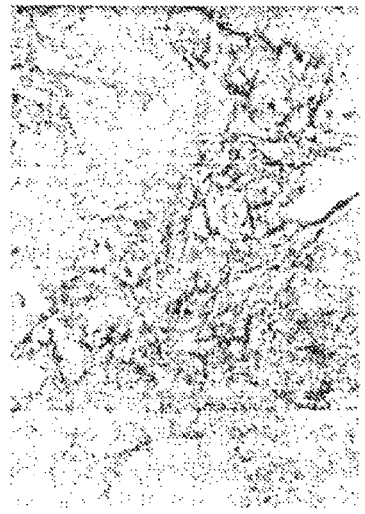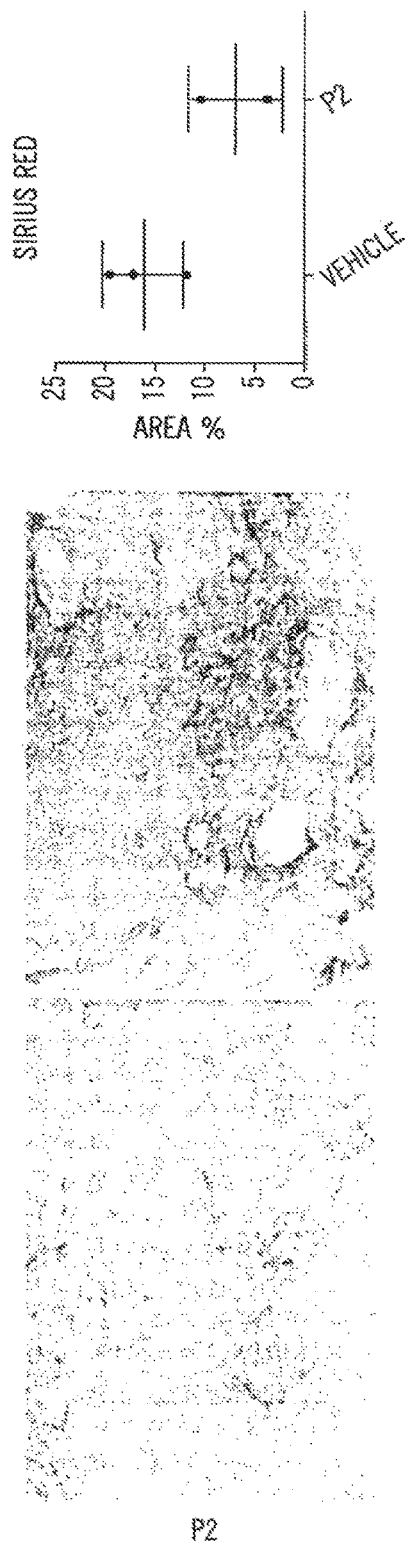
FIG. 11
*IN VIVO* EXPERIMENTS
RESPONSE OF FC1199 TUMORS TO PEPTIDE 2
*MATRIX DEPOSITION*
THE MOUSE GROUP TREATED WITH PEPTIDE SHOWED A REMARKABLE REDUCTION IN MATRIX DEPOSITION AT DAY 13

FIG. 12
IN VIVO EXPERIMENTS
RESPONSE OF FC1199 TUMORS TO PEPTIDE 2 MATRIX DEPOSITION
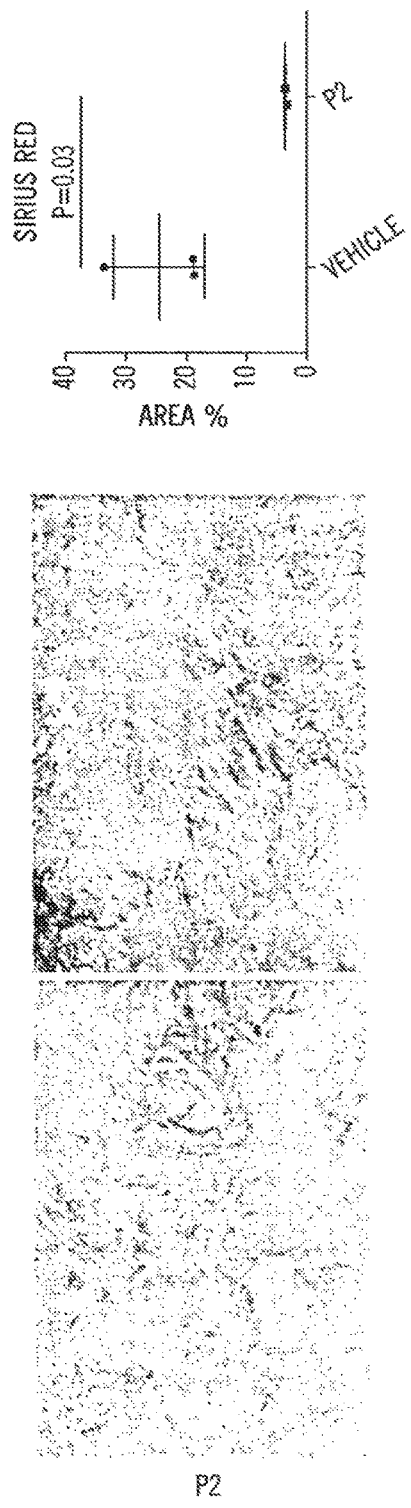
THE MOUSE GROUP TREATED WITH PEPTIDE SHOWED A MARKED REDUCTION MATRIX AT DAY 24

FIG. 13
IN VIVO EXPERIMENTS
RESPONSE OF FC1199 TUMORS TO PEPTIDE 2
CD31
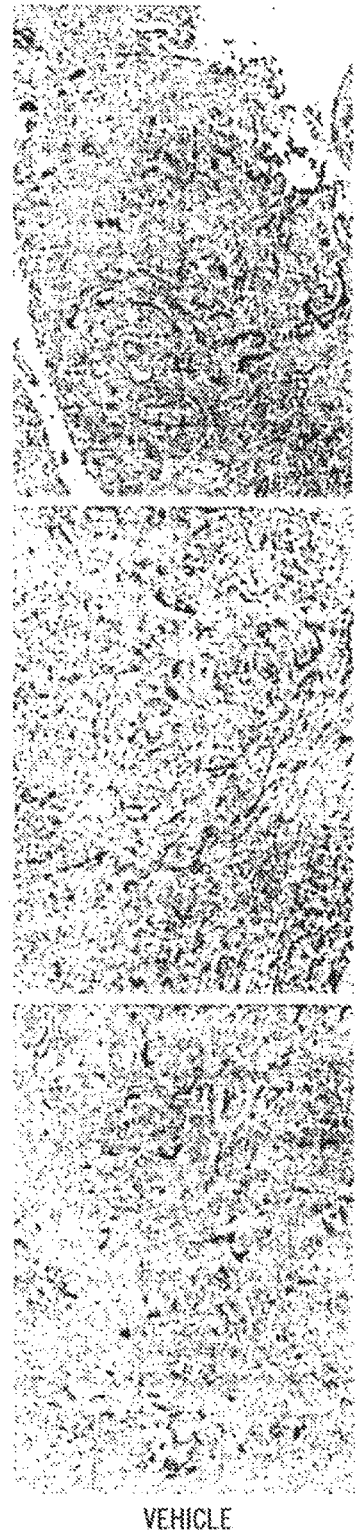
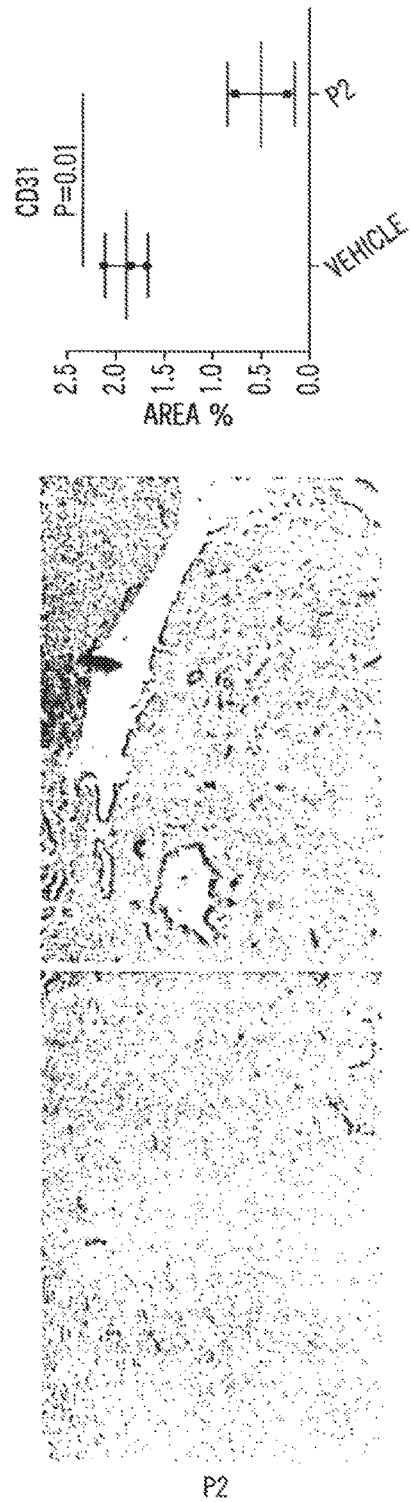
THE MOUSE GROUP TREATED WITH PEPTIDE SHOWED A DRAMATIC REDUCTION IN VESSEL NUMBER/DENSITY AS MEASURED BY THE VESSEL MARKER CD31.

FIG. 14
*IN VIVO* EXPERIMENTS
RESPONSE OF FC1199 TUMORS TO PEPTIDE 2
CD31
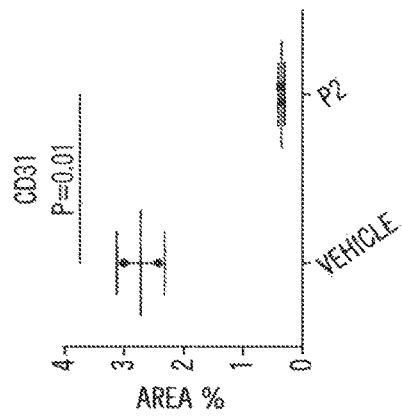
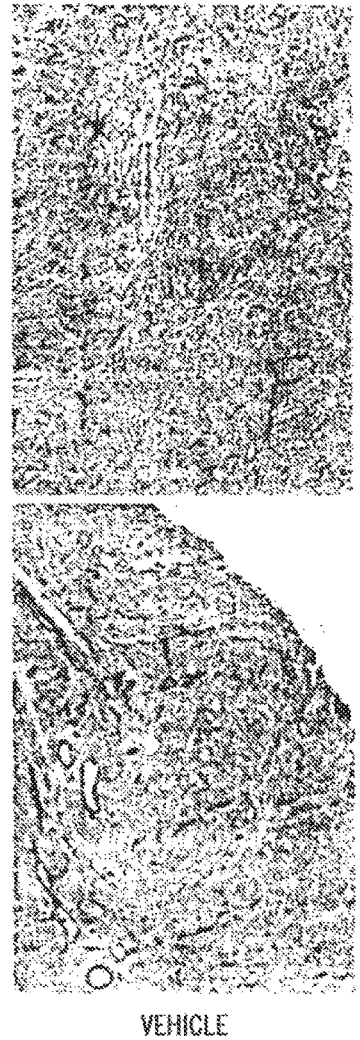
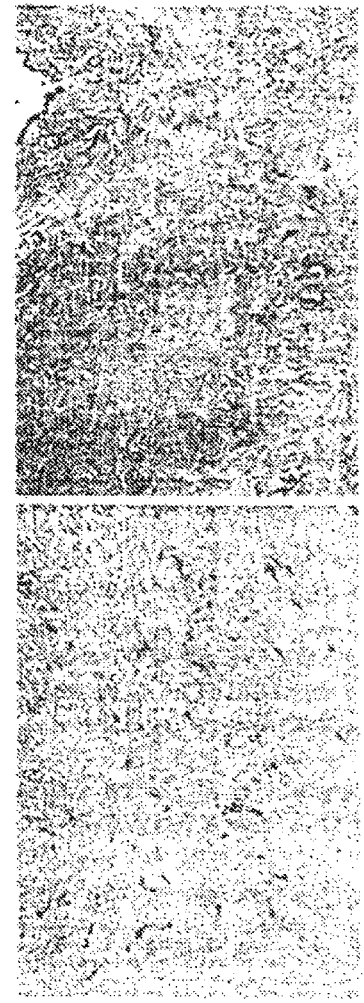
FINAL ANALYSIS (DAY 24)
VEHICLE
P2
THE MOUSE GROUP TREATED WITH PEPTIDE SHOWED A DRAMATIC REDUCTION IN VESSEL NUMBER/DENSITY AS MEASURED BY THE VESSEL MARKER CD31.

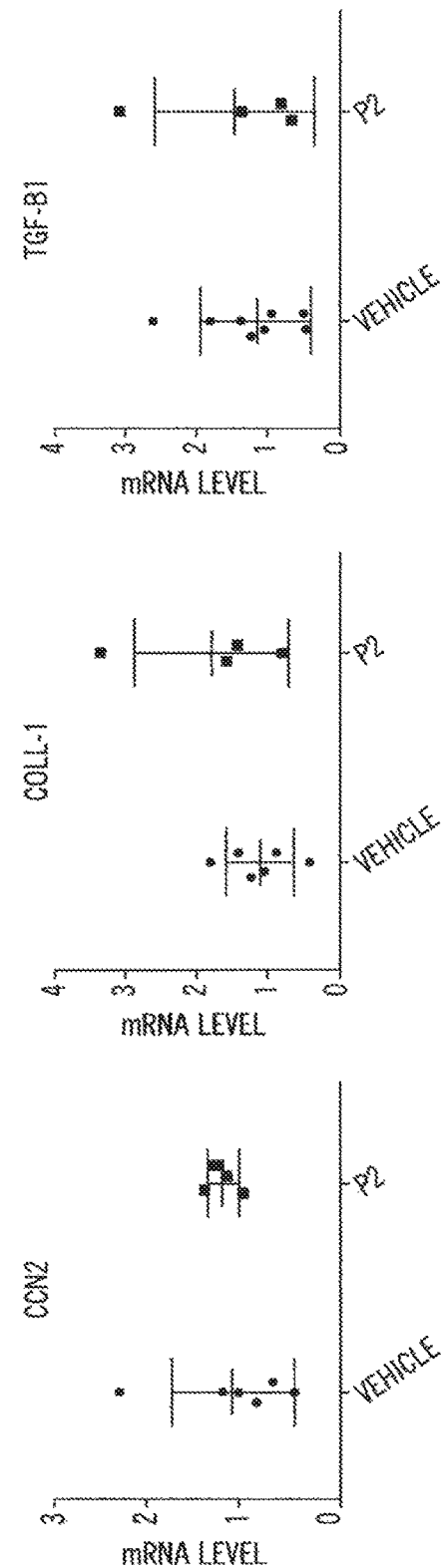

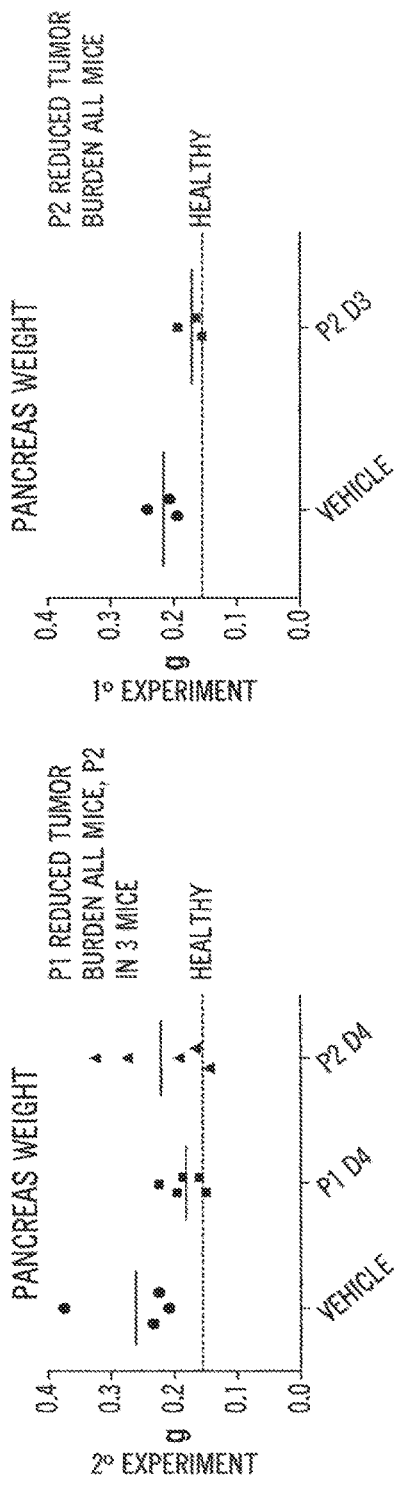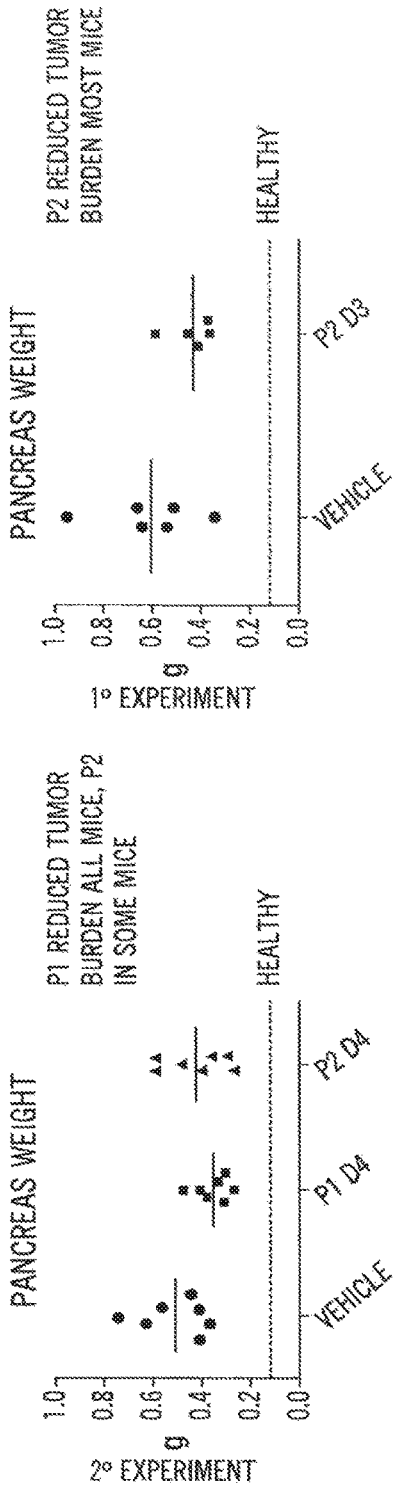

FIG. 18

IN VIVO EXPERIMENTS (EXPERIMENT 2)
RESPONSE OF FC1199 ORTHOTOPIC TUMORS TO PEPTIDE 1 AND 2 ± GEMCITABINE

EXPERIMENTAL GROUPS

1) VEHICLE
2) PEPTIDE 1 (100ng / 200μl, i.p., 3 TIMES PER WEEK)
2) PEPTIDE 2 (100ng / 200μl, i.p., 3 TIMES PER WEEK)
3) GEMCITABINE (40mg / kg, i.p., 2 TIMES PER WEEK)
4) PEPTIDE 1 + GEMCITABINE
5) PEPTIDE 2 + GEMCITABINE

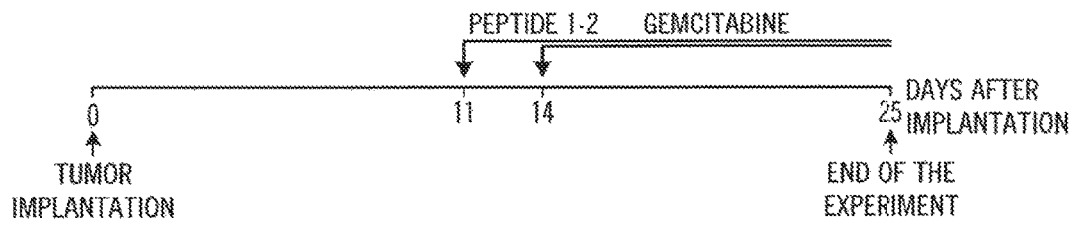

PROTOCOL

FIG. 19 IN VIVO EXPERIMENTS

RESPONSE OF FC1199 ORTHOTOPIC TUMORS TO EARLY TREATMENT
WITH PEPTIDE 1 AND 2

EXPERIMENTAL GROUPS AND PROTOCOL

1) VEHICLE
2) PEPTIDE 1 (100ng / 200μl, i.p., 3 TIMES PER WEEK)
3) PEPTIDE 2 (100ng / 200μl, i.p., 3 TIMES PER WEEK)

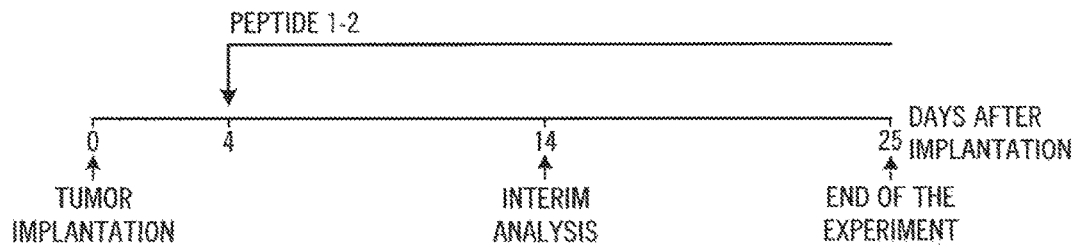

PROTOCOL

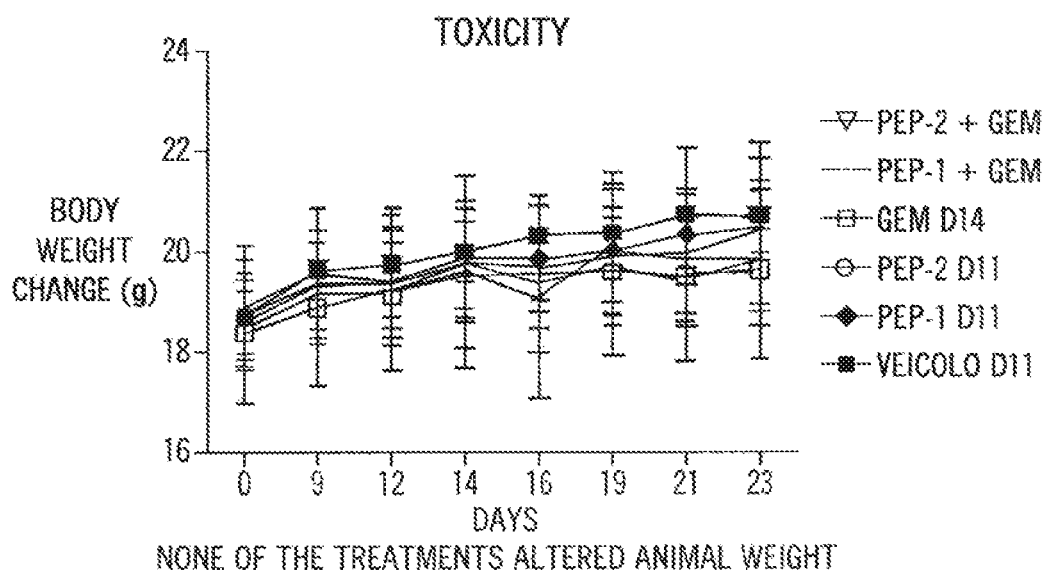

FIG. 21

IN VIVO EXPERIMENTS
RESPONSE OF FC1199 TUMORS TO PEPTIDE 1 AND 2 ± GEMCITABINE
*ANALYSIS (DAY 25)*

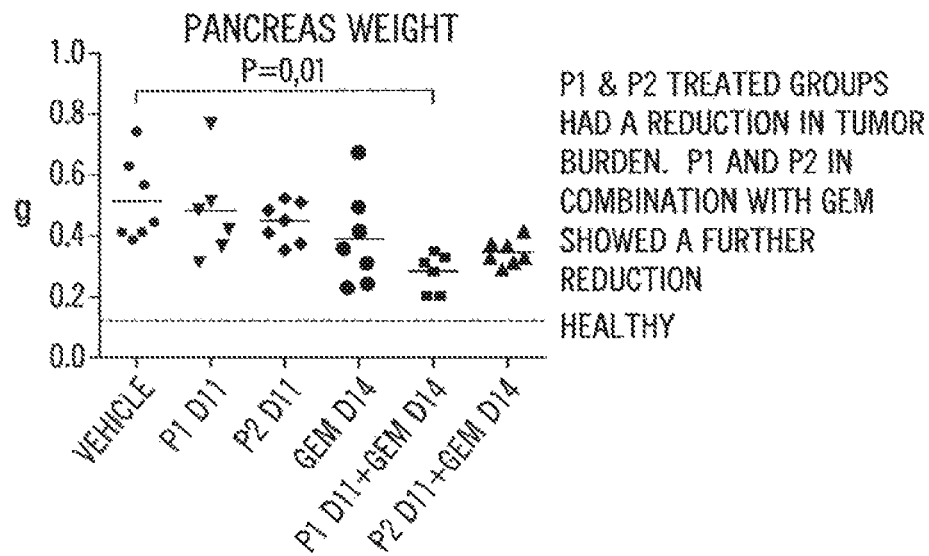

P1 & P2 TREATED GROUPS HAD A REDUCTION IN TUMOR BURDEN. P1 AND P2 IN COMBINATION WITH GEM SHOWED A FURTHER REDUCTION

FIG. 22

IN VIVO EXPERIMENTS
RESPONSE OF FC1199 TUMORS TO PEPTIDE 2 ± GEMCITABINE
*FINAL ANALYSIS (DAY 24)*

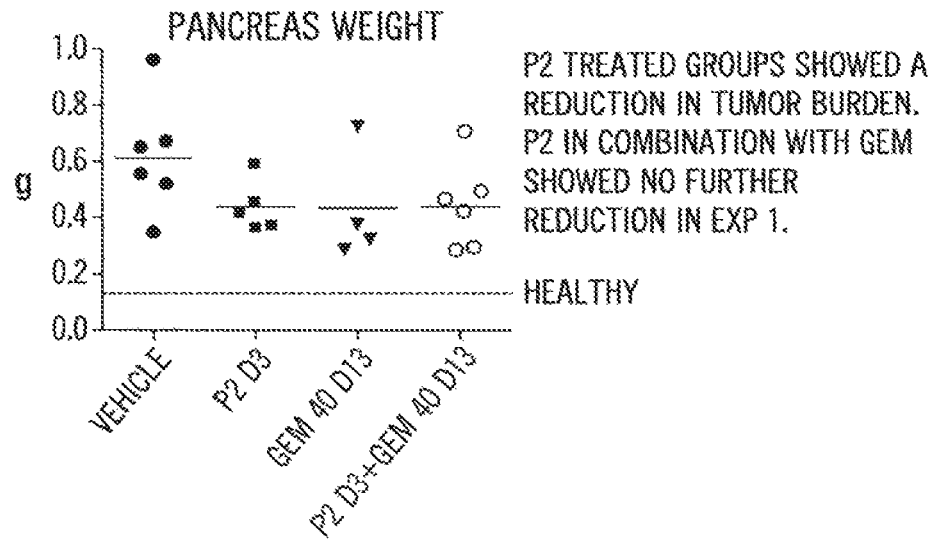

P2 TREATED GROUPS SHOWED A REDUCTION IN TUMOR BURDEN. P2 IN COMBINATION WITH GEM SHOWED NO FURTHER REDUCTION IN EXP 1.

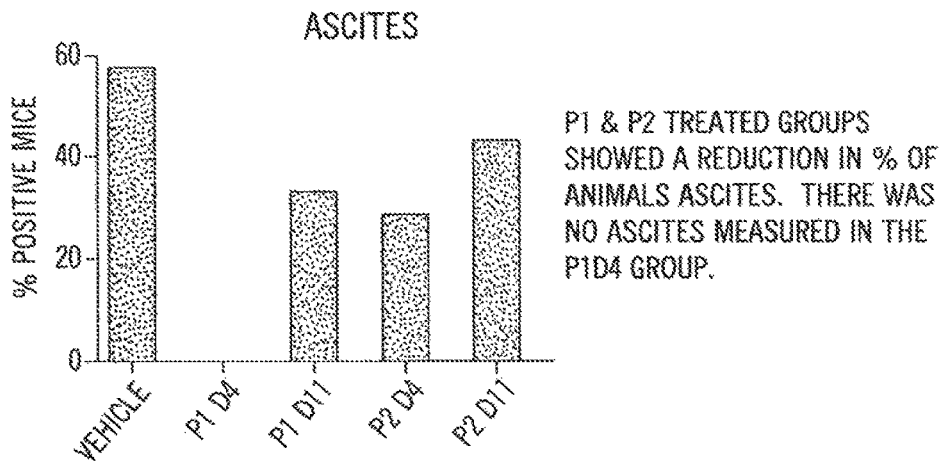

FIG. 23 — IN VIVO EXPERIMENTS
ASCITES PRODUCTION → EFFECT OF PEPTIDE 1 AND 2
ANALYSIS (DAY 25)

P1 & P2 TREATED GROUPS SHOWED A REDUCTION IN % OF ANIMALS ASCITES. THERE WAS NO ASCITES MEASURED IN THE P1D4 GROUP.

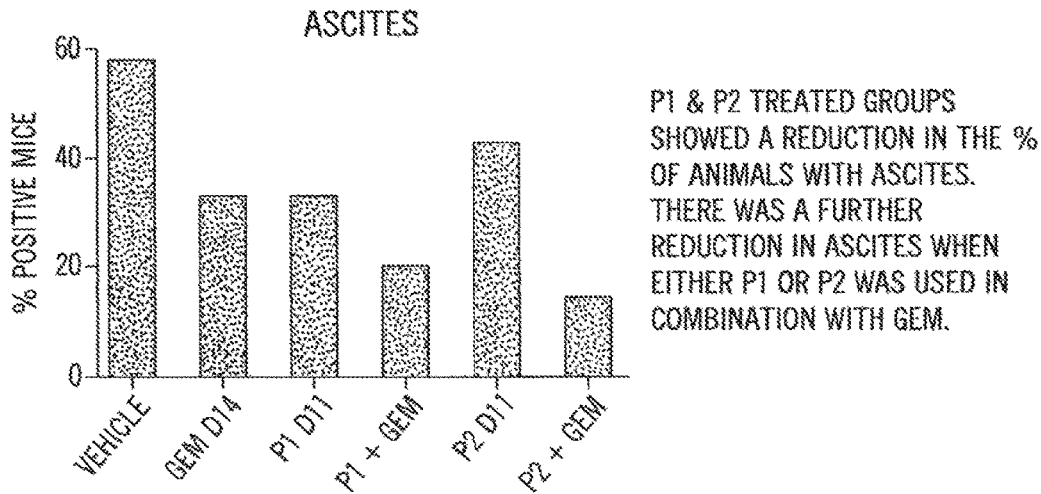

FIG. 24 — IN VIVO EXPERIMENTS
ASCITES PRODUCTION → EFFECT OF PEPTIDE 1 AND 2 ± GEMCITABINE
ANALYSIS (DAY 25)

P1 & P2 TREATED GROUPS SHOWED A REDUCTION IN THE % OF ANIMALS WITH ASCITES. THERE WAS A FURTHER REDUCTION IN ASCITES WHEN EITHER P1 OR P2 WAS USED IN COMBINATION WITH GEM.

METHOD AND KIT FOR TREATING A SOLID TUMOR AND ASSOCIATED DESMOPLASIA

RELATED APPLICATION

This application claims the priority of U.S. Provisional Patent Application No. 62/311,692 filed Mar. 22, 2016, the contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 19, 2017, is named 295792-007126USPT_SL.txt and is 33,581 bytes in size.

BACKGROUND OF THE INVENTION

Field of the Invention

The present invention discloses a method for treating a solid tumor and desmoplasia associated therewith using a combination of a chemotherapeutic agent or an immunotherapy agent and a CCN3-type peptide.

Background

U.S. Pat. No. 7,780,949 by Riser discloses that a full-length CCN3 molecule blocks fibrosis in an in vitro model of renal fibrosis by acting, at least partially, through its ability to down-regulate the profibrotic activity of CCN2. The '949 patent is incorporated in its entirety herein by reference and made a part hereof. CCN3 was not previously known to have activity in fibrosis or wound healing/scarring, either as a positive or negative factor and was not known to have a regulatory effect on CCN2. U.S. Pat. No. 7,780,949 shows that the full-length CCN3 proteins can work to inhibit the production and actions of CCN2, and thus the overproduction of extracellular matrix that characterizes fibrosis in many organs. It is now understood that fibrosis, although initiated by a variety of different insults, once started appears to follow a common pathway apparently always involving one, or both of TGF-beta and CCN2 as causal factors. Therefore, having shown that CCN3 can be used to prevent and or treat fibrosis and abnormal production/accumulation of ECM e.g., collagen, in renal cells and renal disease, one can reasonably assume that it will be useful in such disease in other organs, and even those initiated by different stimuli or insults. U.S. Pat. No. 7,780,949 further discloses measuring CCN3 levels for diagnosis and prognosis of renal disease.

United States Patent Application Publication No. 2007/0059314 discloses the use of CCN3 or CCN3 fragments having angiogenesis-inhibiting activity for the treatment of pathologies requiring such inhibitory activities. The fragments that exhibit angiogenic-inhibiting activity are approximately 40 to approximately 180 amino acids.

Commonly assigned U.S. Pat. No. 9,114,112 discloses a method for treating fibrosis by administering to a human patient an analog CCN3 protein or a fragment thereof. The '112 patent is incorporated in its entirety herein by reference and made a part hereof. Two of the CCN3 fragments disclosed in the '112 patent, CCNp37 and CCNp38, have been found in the present invention to work in combination with a chemotherapeutic agent or an immunotherapeutic agent to treat a solid tumor more effectively than the chemotherapeutic or immunotherapeutic agents alone.

SUMMARY OF THE INVENTION

The present invention provides a kit for treating a human in need thereof having a container of an effective amount of a CCNp37 (SEQ ID No. 37), CCNp38 (SEQ ID No. 38) or a combination of CCNp37 and CCNp38 (SEQ ID Nos. 37 and 38), a container of an effective amount of a chemotherapeutic agent or an immunotherapeutic agent; and instructions for administering these components to a patient in need thereof. In one preferred form of the invention the chemotherapeutic agent is selected from the group consisting of Abraxane, Afinitor, Erlotinib Hydrochloride, Everolimus, 5-FU, Fluorouracil Injection, Gemcitabine Hydrochloride, Gemzar, Irinotecan Hydrochloride Liposome, Mitomycin C, Mitozytrex, Mutamycin, Onivyde, Paclitaxel Albumin-stabilized Nanoparticle Formulation, Sunitinib Malate, Sutent, and Tarceva and combinations of the same. Most preferably the chemotherapeutic agent is gemcitabine. In another form of the invention, the chemotherapeutic agent is a drug combination selected from the group consisting of FOLFIRINOX, GEMCITABINE-CISPLATIN, GEMCITABINE-OXALIPLATIN, and off-label use of drugs for treatment of cancer.

The present invention also provides a method of treating a human patient with a solid tumor with a desmoplasia associated therewith. The method includes the steps of administering to the human patient one or both of peptides of SEQ ID NO. 37 and/or 38 and administering a chemotherapeutic agent or an immunotherapeutic agent to the patient. The method also includes the step of waiting an effective period of time after administration of the peptide or peptides for a reduction in a size of the desmoplasia. Near simultaneous administration of the peptide or peptides and the chemotherapeutic/immunotherapeutic drug is also contemplated. In one preferred form of the invention, the peptide or peptides are administered several times over a period of time and most preferably the peptide or peptide delivery is done prior to administering the chemotherapeutic agent or the immunotherapeutic agent. In one form of the invention, the effective period is from 2 days to 20 days. The method is for treating a solid tumor located on or in or adjacent to a pancreas of the human patient and is cancerous. It is contemplated the methods disclosed herein will also be effective in treating other solid tumors benign or cancerous and more preferably those solid tumors with an associated desmoplasia.

The present invention also provides a kit and a method for reducing a size of a desmoplasia associated with a solid tumor in a human patient by administering to a human patient in need of an effective amount of Peptides 1 and 2 (SEQ ID NOS. 37 and 38).

BRIEF DESCRIPTION OF THE DRAWINGS

FIG. 11 is a series of photomicrographs of matrix deposition on day 13 of the study showing the effects of peptide 2 alone.

FIG. 12 is a series of photomicrographs of matrix deposition on day 24 of the study showing the effects of peptide 2 alone.

FIG. 13 is a series of photomicrographs of vessel number/density on day 13 of the study showing the effects of peptide 2 alone.

FIG. 14 is a series of photomicrographs of vessel number/density on day 24 of the study showing the effects of peptide 2 alone.

FIG. 15 shows the effect of peptide 2 on the mRNA expression on CCN2, COLL-1, and TGF-B1 on day 24 of the study.

FIGS. 16 and 17 show the effects on pancreas weight (tumor burden) in the first and second in vivo tests respectively on day 13 and on day 24.

FIG. 18 shows the experimental group and protocols for in vivo experiments 2 of the response of FC1199 orthotopic tumors to Peptides 1 and 2±gemcitabine.

FIG. 19 shows a toxicity study of peptides 1 and 2±gemcitabine.

FIG. 20 shows experimental groups and protocol for a third in vivo experiment measuring a response of FC1199 orthotopic tumors to Peptides 1 and 2±gemcitabine.

FIGS. 21 and 22 respectively show the results of in vivo experiment of the effects of peptides 1 and 2±gemcitabine on pancreas weight (tumor burden) on day 25 of the study and the results of the second in vivo experiment of the effects of peptide 2±gemcitabine on pancreas weight on day 24.

FIGS. 23 and 24 respectively show the effects of peptides 1 and 2 on ascites production on day 25 of the study and the effects of peptides 1 and 2±gemcitabine on ascites production on day 25 of the study.

DETAILED DESCRIPTION OF THE INVENTION

Figure 1:
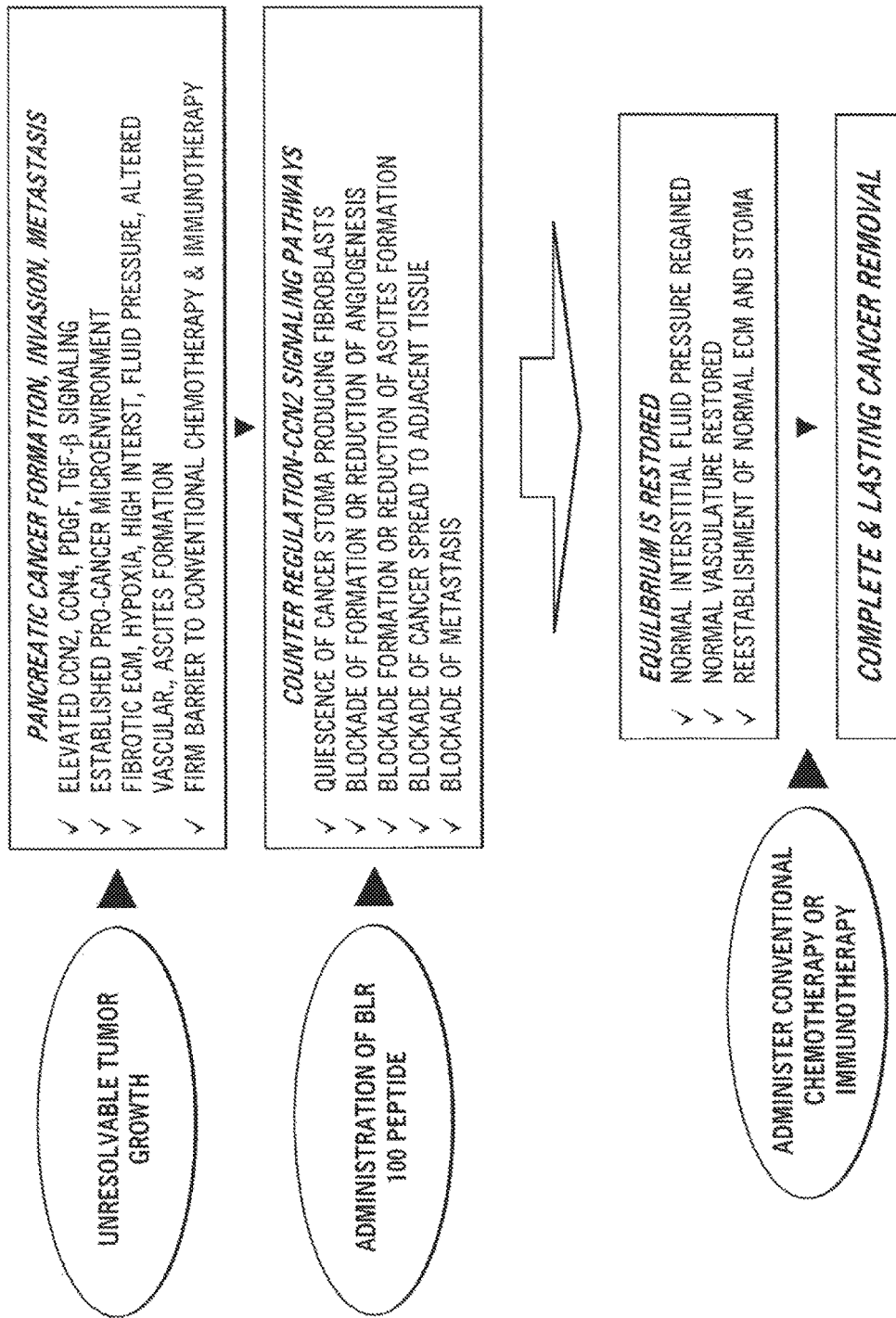
FIG. 1 is a schematic representation of the positive results of our tests showing that peptide 1 (SEQ ID No. 38) and peptide 2 (SEQ ID No. 37) are effective alone or in combination with a chemotherapeutic agent or an immunotherapy agent in treating the stroma or desmoplasia associated with a solid tumor, reducing angiogenesis, reducing ascites formation, and blocking the metastases of the solid tumor.
Figure 2:
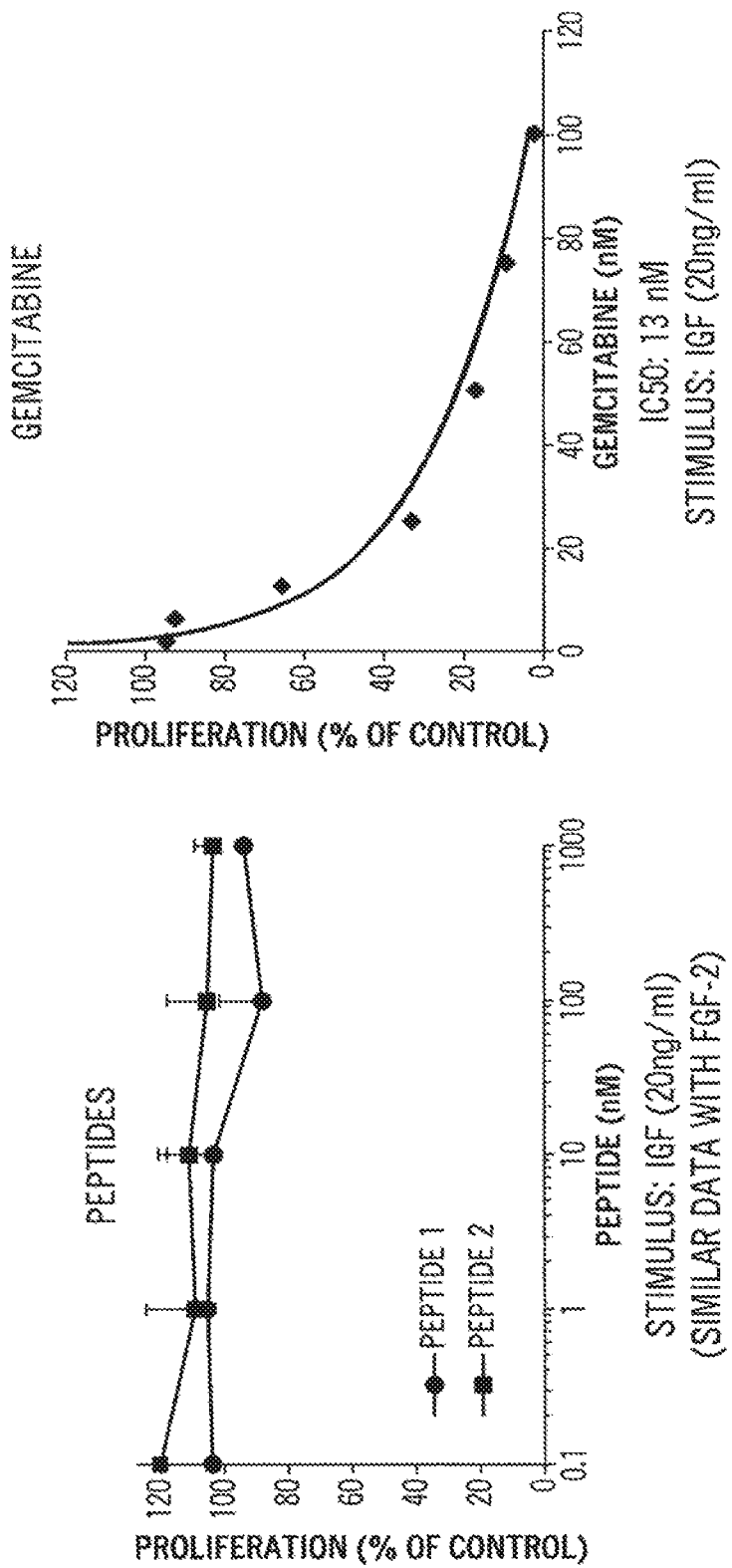
FIG. 2 shows the effects of the peptides and gemcitabine in treating cancer growth in vitro.

While this invention is susceptible of embodiments in many different forms, there is shown in the figures, and will be described herein in detail, specific embodiments thereof with the understanding that the present disclosure is to be considered as an exemplification of the principles of the invention and is not intended to limit the invention to the specific embodiments illustrated.

The present invention is directed to a method of treating pancreatic cancer by administering a combination of a chemotherapeutic agent or an immunotherapeutic agent together with a fragment of a CCN3 protein. In a preferred form of the invention, it was surprisingly found that a small number of peptides having from about 12 to about 20, more preferably 12 to about 18 and most preferably 12 to about 15 amino acids and most preferably 14 amino acids in human, mouse and rat native sequences and in analogs of the same, where native cysteine residues are substituted with a replacement amino acid, are able to mimic specific activities of CCN3. In a preferred form of the invention, the replacement amino acids are selected from serine, alanine, glycine, S-methylated cysteine or a combination thereof. Most preferably, the replacement amino acid is serine. These short peptides are far smaller than the full-length CCN3 protein, the naturally occurring one-half and one-quarter length CCN3 fragments reported in the literature, and the artificially prepared 40 to 180 amino acid fragments disclosed in the '314 published patent application discussed above, and are likely to be more easily synthesized and formulated for delivery to a patient in need thereof. Sometimes these small peptides may be referred to as "CCNp" followed by a number, e.g., CCNp38.

The peptides can optionally have functional groups to assist in targeting, to increase the half-life in vivo, and other functions. Suitable functional groups include glycol groups, polyethylene glycol (PEG), proteins, including serum proteins, and glycans. Glycans can be added through a process such as glycosylation. Glycosylation includes N-linked glycosylation, O-linked glycosylation, phospho-serine glycosylation, C-mannosylation, and glypiation.

These peptides are more fully explained in U.S. Pat. No. 9,114,112.

The following table shows the peptide sequences by number. The peptide numbers are retained from the commonly assigned U.S. Pat. No. 9,114,112. It is contemplated that all of the sequences listed in the table will be effective in the methods and kits disclosed herein.

| SEQ. ID. NO. | DESCRIPTION | SEQUENCE |
| --- | --- | --- |
| 37 | Mouse analog with native cysteines replaced with serines | FSGVSSDGRSSTPH |
| 38 | Mouse analog with native cysteines replaced with serines | SDRSADPNNQTGIS |
| 48 | Human and mouse native CCNp37 | FCGVCSDGRCCTPH |
| 49 | Mouse native CCNp38 | CDRSADPNNQTGIC |
| 50 | Human native CCNp38 | CDRSADPSNQTGIC |
| 52 | Rat native CCNp38 | CDRSADPNNETGIC |

-continued

| SEQ. ID. NO. | DESCRIPTION | SEQUENCE |
|---|---|---|
| 53 | Rat analog CCNp38 with native cysteines replaced with serines | SDRSADPNNETGIS |
| 54 | Human or mouse analog CCNp37-14 with native cysteines replaced with serines and without FS on N-terminal end | GVSSDGRSSTPH |
| 55 | Human or mouse analog CCNp37-15 with native cysteines replaced with serines and without PH on C-terminal end | FSGVSSDGRSST |
| 56 | Human analog CCNp38-3 with native cysteines replaced with serines | SDRSADPSNQTGIS |
| 57 | Human analog CCNp38-9 with native cysteines replaced with serines and minus CD (or SD) at N-terminal end | RSADPSNQTGIS |
| 58 | Human analog CCNp38-10 with native cysteines replaced with serines and with added T on C-terminal end | SDRSADPSNQTGIS-T |
| 59 | Mouse analog CCNp38-7 with native cysteines replaced with serines and without CD or (SD) at N-terminal end | RSADPNNQTGIS |
| 60 | Rat analog CCNp38-8 with native cysteines replaced with serines and without CD or (SD) at N-terminal end | RSADPNNETGIS |
| 61 | Human native CCNp38-11 with a T added to the C-terminal end | SDRSADPSNETGIS-T |

It is also contemplated that the cysteine residues could also be replaced by alanine, glycine, S-methylated cysteine or combinations thereof (including serine) to produce similar activity.

In Vitro and In Vivo Studies on Pancreatic Cells and Tumors

FIGS. 1-24 show the in vitro and in vivo studies of CCNp37 (SEQ ID NO. 37) (Peptide 2 in the FIGS.) and CCNp38 (SEQ ID NO. 38) (Peptide 1 in the FIGS.) alone or in combination with a chemotherapeutic agent gemcitabine in treating pancreatic cells or orthotopic tumors implanted in the pancreas of mice. Gemcitibine is an example of an approved small molecule chemotherapeutic agent that is used in the clinic for pancreatic cancer, other suitable chemotherapeutic or immunotherapeutic agents are, for example, Abraxane (Paclitaxel Albumin-stabilized Nanoparticle Formulation), Afinitor (Everolimus), Erlotinib Hydrochloride, Everolimus, 5-FU (Fluorouracil Injection), Fluorouracil Injection, Gemcitabine Hydrochloride, Gemzar (Gemcitabine Hydrochloride), Irinotecan Hydrochloride Liposome, Mitomycin C, Mitozytrex (Mitomycin C), Mutamycin (Mitomycin C), Onivyde (Irinotecan Hydrochloride Liposome), Paclitaxel Albumin-stabilized Nanoparticle Formulation, Sunitinib Malate, Sutent (Sunitinib Malate), and Tarceva (Erlotinib Hydrochloride) and combinations of the same. Other suitable drug combinations for treating pancreatic cancer includes: FOLFIRINOX, GEMCITABINE-CIS-PLATIN, GEMCITABINE-OXALIPLATIN, and OFF. Suitable drugs for treatment for gastroenteropancreatic neuroendocrine tumors: Lanreotide Acetate, and Somatuline Depot (Lanreotide Acetate).

FIG. 1 shows an overview of the results indicating that Peptides 1 and 2 were effective in treating desmoplasia or stroma associated with a solid tumor, reducing angiogenesis, reducing the formation of ascites associated with a solid tumor and blocking the expansion and spread of the tumor and cancer cells. Depending on the need conventional chemotherapeutic or immunotherapeutic drugs may also be used in combination with the peptides for better effectiveness, and at lower dosing levels of conventional chemotherapeutic or immunotherapeutic drugs, since with the removal or reconstruction of the cancer stroma/desmoplasia they will become more effective. Lower dosing has the advantage of reducing adverse side effects that are known to occur from administering chemotherapeutic/immunotherapeutic agents and potentially reduce the cost of these drugs.

Peptides were examined in two different pancreatic cancer cell lines to determine consistency of response. We sought to determine if there was efficacy of the peptide alone, or in combination with conventional chemotherapy, i.e., does it potentiate the effects of current therapy. The two cell lines used were Human MIA PaCa2-Luc, and Murine FC1199 (derived from tumors in KPC GEM mice).

Peptides 1 and 2 alone did not slow cancer growth in vitro but gemcitibine did, as expected since it is a cytotoxic drug (FIGS. 2-5). Peptides 1 and 2 did little or nothing to potentiate the effects of the chemotherapeutic agent gemcitabine in reducing cancer growth in vitro (FIGS. 2-5).

Figure 3:
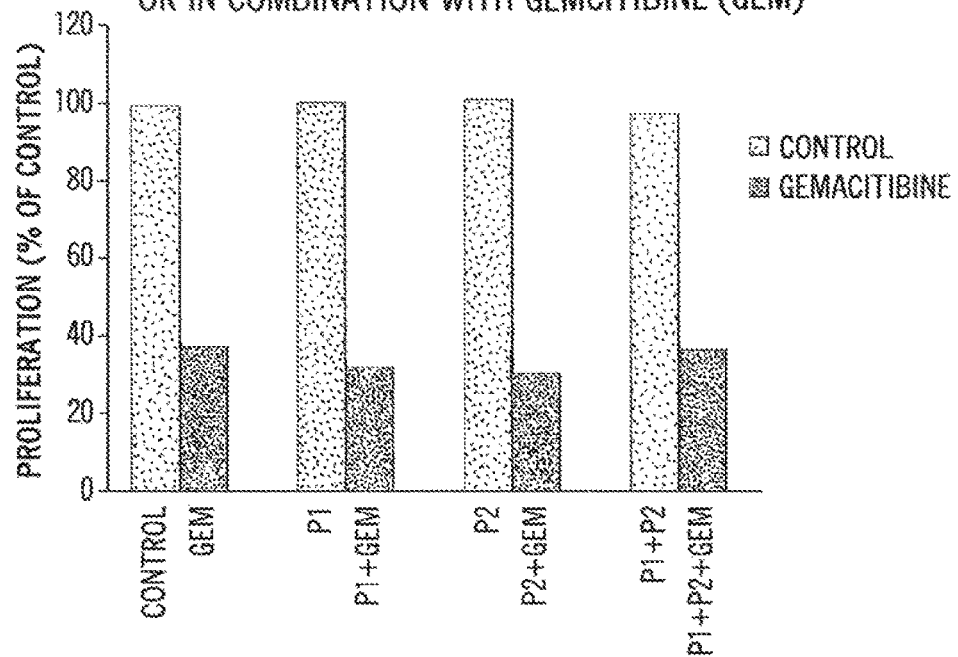
FIG. 3 shows the effects of the peptides alone or in combination with one another or in combination with gemcitabine in treating cancer cell growth in vitro.
Figure 4:
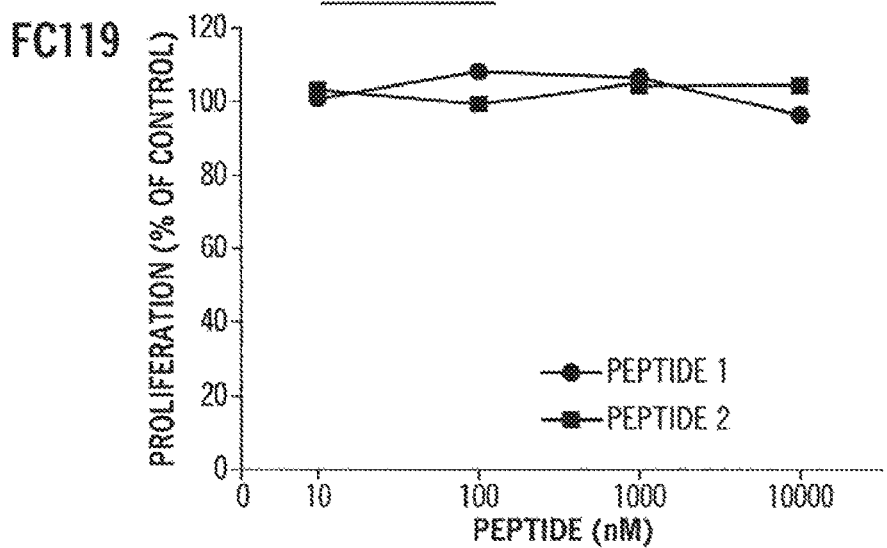
FIG. 4 shows the effect of the peptides on the proliferation of cancer cell FC1199 in vitro.
Figure 5:
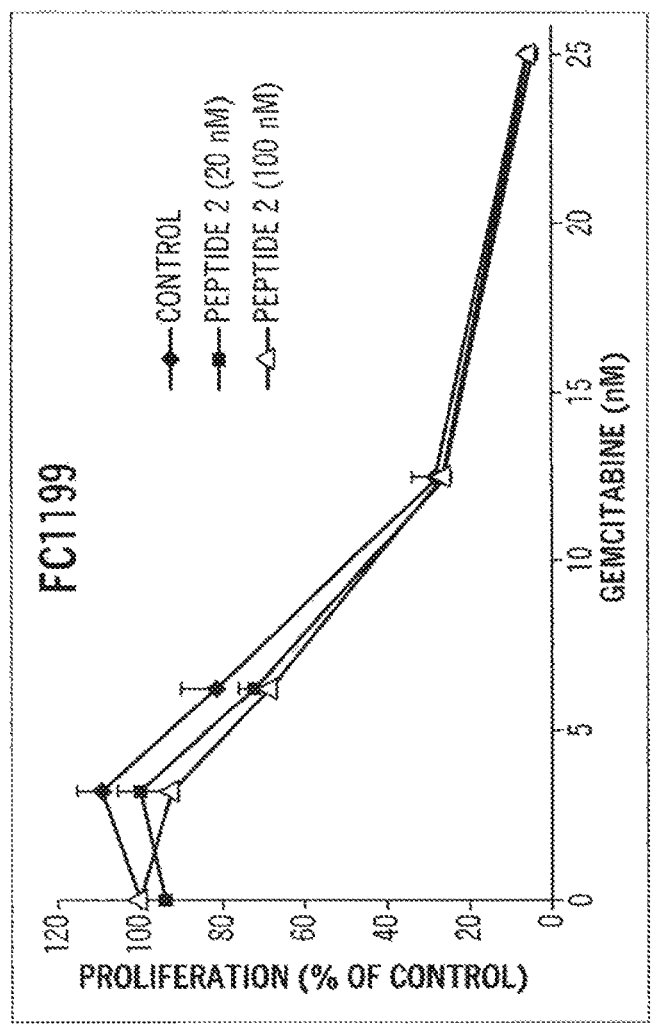
FIG. 5 shows the effect of peptide 2 on gemcitabine repression of FC1199 growth in vitro.

While not wishing to be bound to any particular theory, it was hypothesized that the peptides might still be effective in blocking the formation and/or removing the formation of desmoplasia or tumor stroma associated with a solid tumor alone acting to prevent and or to treat cancer and as well to providing greater access of the chemotherapeutic or immunotherapeutic agent to the tumor. Additionally, Peptides 1 and 2 can be combined with small molecule drugs such as gemcitabine without adverse effect (FIGS. 3 and 5). It is believed that many large, and smaller, molecule immunotherapeutic agents will not react with Peptides 1 and 2 and they may also be used in combination with one another. While the in vitro studies show that Peptides 1 and 2 do not reduce the proliferation of MIA PaCa2-Luc cancer cells (FIG. 2), the in vivo studies show surprisingly that they are effective in reducing the growth of orthotopic FC1199 tumor burden as measured by pancreas weight (FIGS. 11, 12, 18, 19, 21, and 22), and a reduction in desmoplasia as measured by matrix deposition area (FIGS. 13 and 14), a reduction in angiogenesis as measured by vessel number/vessel density (FIGS. 15 and 16).

The in vitro studies used human MIA PaCa2-Luc, and Murine FC1199 cell lines. The results of the in vitro studies show that Peptides 1 and 2 do not have an effect in cell proliferation (FIGS. 2-4) and did not potentiate the effects of gemcitabine in repressing of FC1199 cell growth (FIGS. 3 and 5).

Figure 6:
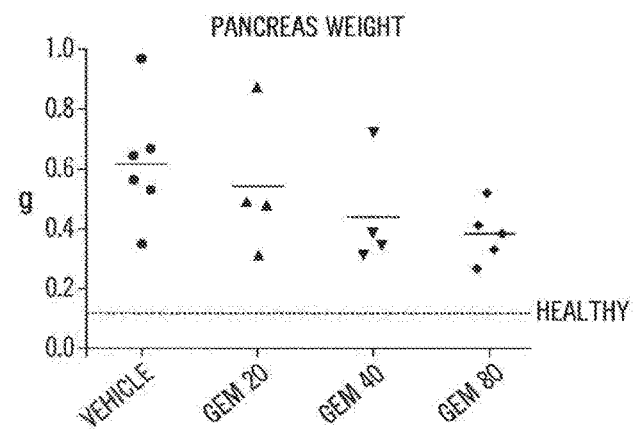
FIG. 6 shows the response of FC1199 tumors to gemcitabine in vivo.
Figure 7:
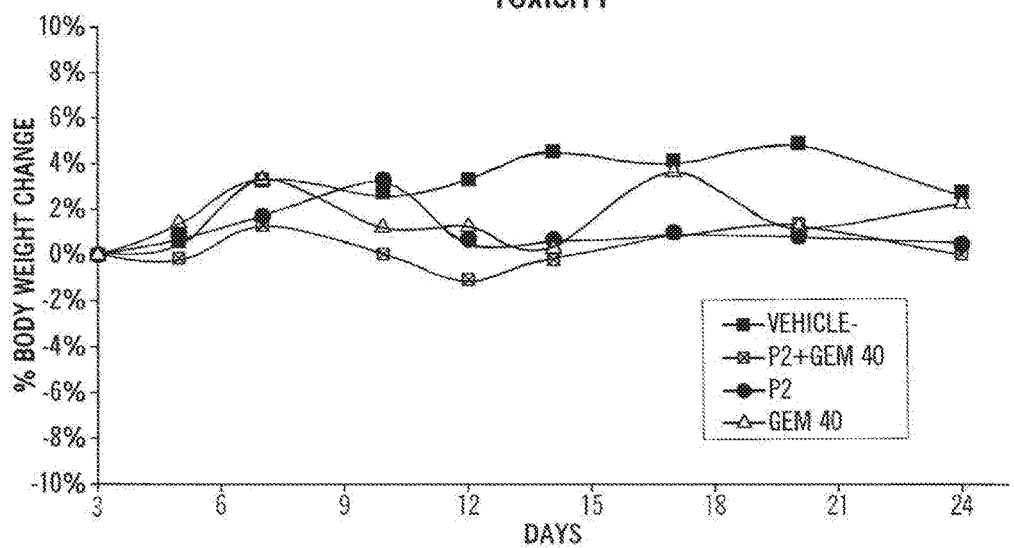
FIG. 7 shows a toxicity study of peptide 2±gemcitabine.
Figure 8:
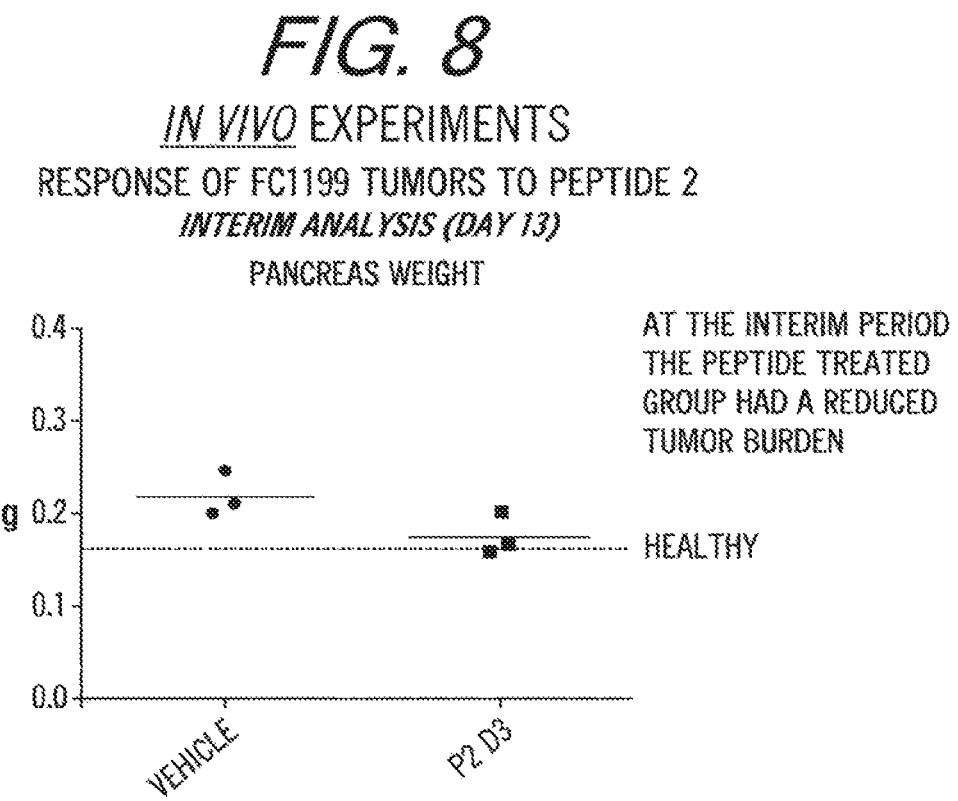
FIG. 8 shows the response of FC1199 orthotopic tumors to peptide 2 on day 13 of the study.
Figure 9:
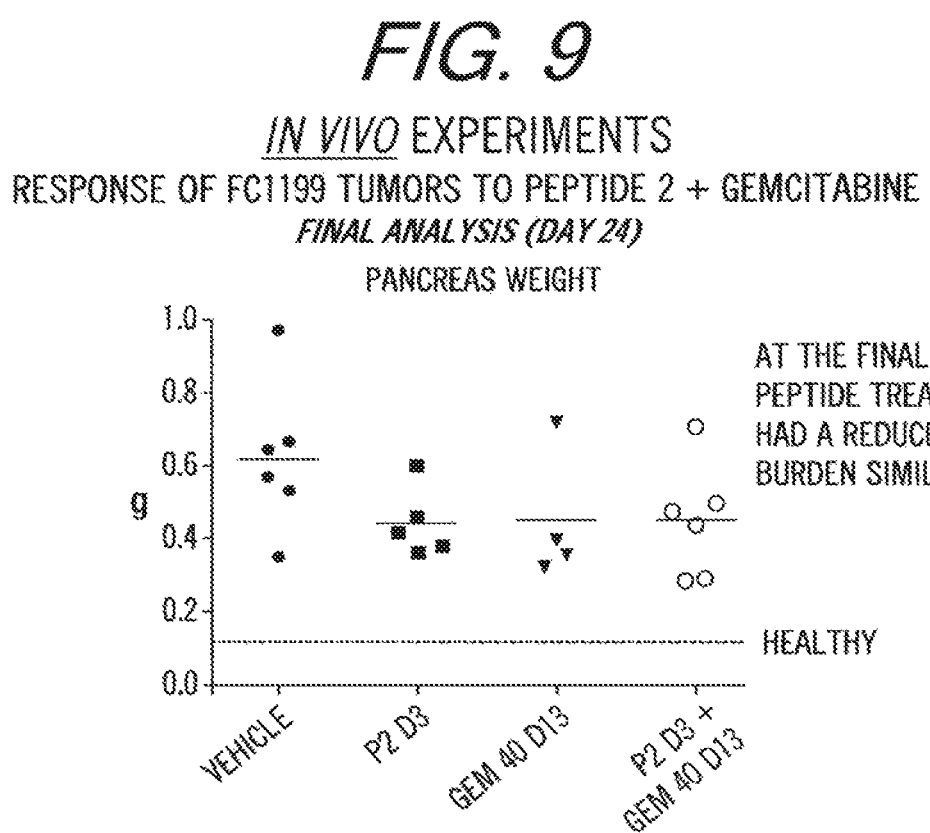
FIG. 9 shows the response of FC1199 orthotopic tumors to peptide 2±gemcitabine on day 24 of the study.
Figure 10:
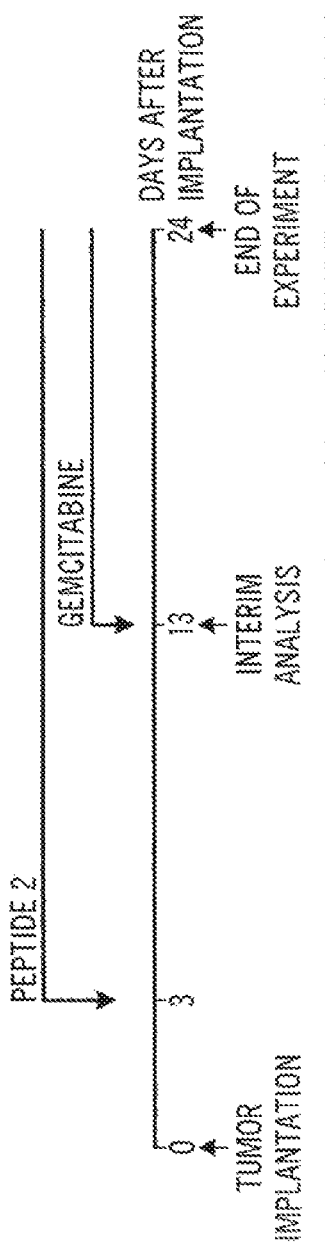
FIG. 10 shows the experimental group and protocols for in vivo experiments of the response of FC1199 orthotopic tumors to Peptide 2±gemcitabine.

FIGS. 6-24 show the experimental protocol and results of in vivo studies of orthotopic tumors derived from the Murine FC1199 cell line and implanted into Kras and P53 mice. Gemcitabine produces a dose-dependent response to tumor burden as measured by pancreas weight (FIG. 6). FIG. 10 shows the protocol of a first in vivo study (Experiment 1) where Peptide 2 was administered to the mice on day 3 of the study after tumor implantation, an interim analysis was conducted on day 13 to determine the effect of Peptide 2, gemcitabine was then administered on day 13 and the combined results of Peptide 2 and gemcitabine were measured on day 24 (FIG. 10). FIG. 7 shows that Peptide 2±gemcitabine were non-toxic. FIG. 8 shows on day 13, Peptide 2 reduced the tumor growth in terms of a lighter pancreas weight compared to the control. FIG. 9 shows the results of Peptide 2±gemcitabine on day 24 in reducing cancer tumor growth in terms of pancreas weight when compared to a vehicle control and was comparable to gemcitabine. FIGS. 13 and 14 show the effects of administering Peptide 2 in reducing the matrix deposition (desmoplasia) respectively on day 13 (early) and 24 (later) when compared to the control. Thus, Peptide 2 reduces the desmoplasia associated with a solid tumor when compared to a vehicle control.

FIGS. 13 and 14 show the effects of Peptide 2 on vessel number/vessel density respectively on day 13 and day 24 showing a reduction in the vessel density when compared to a control. Thus, Peptide 2 reduces angiogenesis associated with a solid tumor.

FIGS. 18 and 19 show the protocol of a second in vivo experiment (Experiment 2). FIG. 19 shows where Peptides 1 and Peptide 2 were administered on day 4 without the administration of gemcitabine. Peptides 1 and 2 are both effective in reducing tumor growth and weight, the data also show these two molecules do not have identical effect and sense they come from two different regions of the CCN3 molecule, both being shown to have anti-fibrotic activity, then the use of these peptides in combination would be expected to have an augmented effect. FIG. 18 shows the in vivo protocol where Peptides 1 and 2 were administered on day 11 and gemcitabine was administered on day 14. FIGS. 16 and 17 show that both peptides on day 14 and day 25 were effective in reducing the tumor burden in terms of reduced pancreas weight when compared to a control.

FIGS. 21-24 show the protocol for the second invo experiment on the effectiveness of administering Peptides 1 and 2±gemcitabine. In FIG. 20 it shows that the administration of Peptides 1 and 2 with gemcitabine were non-toxic based on body weight change. In FIG. 21, peptide 1 or 2 was delivered on day 11 of the study after tumor implantation and gemcitabine was delivered on day 14. FIG. 19 shows that all of the experimental groups were non-toxic. FIGS. 21-22 show that the experimental groups of Experiment 1 and Experiment 2 were effective in reducing tumor growth when compared to a control. FIGS. 21 and 22 show that Peptides 1 and 2 can potentiate the therapeutic effects of the standard chemotherapeutic agent gemcitabine. FIGS. 23 and 24 show Peptides 1 and 2 were effective in reducing the number of mice with ascites and FIG. 24 shows that Peptides 1 and 2±gemcitabine were effective in reducing the number of mice with ascites when compared to a control. FIG. 23 shows that the earlier the administration of the peptides the greater the impact on reducing ascites production. Also the combination of Peptide 1 with gemcitabine and Peptide 2 with gemcitabine were more effective in reducing ascites then the use of gemcitabine alone. These data also demonstrate that Peptide 1 and 2 reduce inflammation. Ascites formation is a marker of late stage pancreatic cancer and can predict mortality.

The present invention also provides a method for treating and a kit for delivering Peptide 1 or Peptide 2 to a patient with a solid tumor for reducing the desmoplasia associated with the solid tumor. The method and kit would include a container of an effective amount of one or both of the Peptides 1 and/or 2 and instructions for administering the peptide(s) by any route of administration set forth herein including intravenous, intramuscular, subcutaneous, nasal, topical, vaginal, anal, transdermal, inhalation, oral, buccal, intraperitoneal, intraosseous and combinations of the same. The peptides, in one form of the invention, is in a lyophilized form or a liquid form and are reconstituted in the first instance or brought to the appropriate concentration in the second instance and then administered to the patient in need thereof.

The present invention also provides a method and a kit for administering Peptide 1, Peptide 2, or Peptides 1 and 2, in combination with a chemotherapeutic agent or an immunotherapeutic agent to a patient with a solid tumor and desmoplasia associated with the solid tumor. The kit would include a container of an effective amount of the peptide or peptides and a container with the chemotherapeutic agent or the immunotherapeutic agent together in medical packaging with written instructions for administering the components of the kit. The method would include administering one or both of the peptides to the patient and then waiting an effective period of time for a reduction in desmoplasia, say 2 days to 20 days for example, and then administering the chemotherapeutic agent or an immunotherapeutic agent to the patient. It is contemplated the peptides and chemotherapeutic/immunotherapeutic agent could also be delivered in combination on one or both administrations. It is also contemplated the peptides could be administered several times over a period of time prior to administering the chemotherapeutic agent or an immunotherapeutic agent, alone or together with the peptides, to the patient and that containers are provided for each administration. It is also contemplated that the dose of the chemotherapeutic or immunotherapeutic that may be required to completely treat the tumor will be less than that used alone or in combination with other chemotherapeutic or immunotherapeutic agents without these peptides or without a peptide pretreatment.

The practice of the present invention will employ and incorporate, unless otherwise indicated, conventional techniques of cell biology, cell culture, molecular biology, microbiology, genetic engineering and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

The invention claimed is:

1. A kit for treating a human with a solid tumor with desmoplasia comprising:
   a container of an effective amount of a CCNp37 (SEQ ID No. 37), CCNp38 (SEQ ID No. 38) or a combination of CCNp37 and CCNp38 (SEQ ID Nos. 37 and 38);
   a container of an effective amount of a chemotherapeutic agent or an immunotherapeutic agent; and
   instructions for administering these components to a patient in need thereof.

2. The kit of claim 1 wherein the chemotherapeutic agent is gemcitabine.

3. The kit of claim 1 wherein the chemotherapeutic agent is selected from the group consisting of Abraxane, Afinitor, Erlotinib Hydrochloride, Everolimus, 5-FU, Fluorouracil Injection, Gemcitabine Hydrochloride, Gemzar, Irinotecan Hydrochloride Liposome, Mitomycin C, Mitozytrex, Mutamycin, Onivyde, Paclitaxel Albumin-stabilized Nanoparticle Formulation, Sunitinib Malate, Sutent, and Tarceva and combinations of the same.

4. The kit of claim 1 wherein the chemotherapeutic agent is a drug combination selected from the group consisting of FOLFIRINOX, GEMCITABINE-CISPLATIN and GEMCITABINE-OXALIPLATIN.

5. A method of treating a human patient with a solid tumor with a desmoplasia associated therewith comprising:
   administering to the human patient one or both of peptides of SEQ ID NO. 37 and/or 38 and administering a chemotherapeutic agent or an immunotherapeutic agent to the patient.

6. The method of claim 5 further comprising the step of waiting an effective period of time after administration of the peptide or peptides for a reduction in a size of the desmoplasia.

7. The method of claim 5 further comprising the step of waiting an effective period of time after administration of the peptide or peptides for a reduction in a density of the desmoplasia.

8. The method of claim 5 further comprising the step of waiting an effective period of time after administration of the peptide or peptides for a reduction in blood vessels associated with the desmoplasia prior to administering the chemotherapeutic agent.

9. The method of claim 6 wherein the peptide or peptides are administered several times over a period of time.

10. The method of claim 9 wherein the step of administering the peptide or peptides several times over a period of time occurs prior to administering the chemotherapeutic agent.

11. The method of claim 5 wherein the effective period is from 2 days to 20 days.

12. The method of claim 5 wherein the chemotherapeutic agent is gemcitabine.

13. The method of claim 5 wherein the chemotherapeutic agent is selected from the group consisting of Abraxane, Afinitor, Erlotinib Hydrochloride, Everolimus, 5-FU, Fluorouracil Injection, Gemcitabine Hydrochloride, Gemzar, Irinotecan Hydrochloride Liposome, Mitomycin C, Mitozytrex, Mutamycin, Onivyde, Paclitaxel Albumin-stabilized Nanoparticle Formulation, Sunitinib Malate, Sutent, and Tarceva and combinations of the same.

14. The method of claim 5 wherein the chemotherapeutic agent is selected from a drug combination selected from the group consisting of FOLFIRINOX, GEMCITABINE-CISPLATIN, and GEMCITABINE-OXALIPLATIN.

15. The method of claim 5 wherein the solid tumor is on a pancreas of the human patient.

16. The method of claim 13 wherein the solid tumor is cancerous.

17. A method for treating a desmoplasia associated with a solid tumor in a human patient comprising administering to the patient an effective amount of CCNp37 (SEQ ID No. 37), CCNp38 (SEQ ID No. 38) or a combination of CCNp37 and CCNp38 (SEQ ID Nos. 37 and 38).

18. The method of claim 17 further comprising delivering a peptide or peptides several times over a period of time.

* * * * *

SEQUENCE LISTING

```
<160> NUMBER OF SEQ ID NOS: 67

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ser Leu Phe Leu Arg Lys Arg Ser Leu Ser Leu Gly Phe Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Gly Phe Leu Leu Phe His Leu Leu Ser Gln Val Ser Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gln Val Ser Ala Ser Leu Arg Ser Pro Ser Arg Ser Pro Pro
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Pro Ser Arg Ser Pro Pro Lys Ser Pro Ser Ile Ser Pro Thr
1               5                   10                  15

Ser Ala

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 5

Ser Pro Thr Ser Ala Pro Gly Val Arg Ser Val Leu Asp Gly Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Leu Asp Gly Ser Ser Ser Ser Pro Val Ser Ala Arg Gln Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Arg Gln Arg Gly Glu Ser Ser Ser Glu Met Arg Pro Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Met Arg Pro Ser Asp Gln Ser Ser Gly Leu Tyr Ser Asp Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Ser Asp Arg Ser Ala Asp Pro Asn Asn Gln Thr Gly Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gln Thr Gly Ile Ser Met Val Pro Glu Gly Asp Asn Ser Val
1               5                   10                  15

<210> SEQ ID NO 11
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Gly Asp Asn Ser Val Phe Asp Gly Val Ile Tyr Arg Asn Gly Glu
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Arg Asn Gly Glu Lys Phe Glu Pro Asn Ser Gln Tyr Phe
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Tyr Phe Ser Thr Ser Arg Asp Gly Gln Ile Gly Ser Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ile Gly Ser Leu Pro Arg Ser Gln Leu Asp Val Leu Leu Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Leu Leu Pro Gly Pro Asp Ser Pro Ala Pro Arg Lys Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Pro Arg Lys Val Ala Val Pro Gly Glu Ser Ser Glu Lys
1               5                   10
```

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Glu Lys Trp Thr Ser Gly Ser Asp Glu Gln Gly Thr Gln Gly
1               5                   10                  15

Thr

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Glu Gln Gly Thr Gln Gly Thr Leu Gly Gly Leu Ala Leu Pro
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ala Leu Pro Ala Tyr Arg Pro Glu Ala Thr Val Gly Val
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Thr Val Gly Val Glu Val Ser Asp Ser Ser Ile Asn Ser Ile
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ile Asn Ser Ile Glu Gln Thr Thr Glu Trp Ser Ala Ser Ser
1               5                   10                  15

<210> SEQ ID NO 22
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 22

Trp Ser Ala Ser Ser Lys Ser Ser Gly Met Gly Val Ser Thr Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Ser Thr Arg Val Thr Asn Arg Asn Arg Gln Ser Glu Met
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Gln Ser Glu Met Val Lys Gln Thr Arg Leu Ser Ile Val Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Ser Ile Val Arg Pro Ser Glu Gln Glu Pro Glu Glu Val Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Glu Glu Val Thr Asp Lys Lys Gly Lys Lys Ser Leu Arg Thr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Leu Arg Thr Lys Lys Ser Leu Lys Ala Ile His Leu Gln
1               5                   10                  15
```

```
<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ile His Leu Gln Phe Glu Asn Ser Thr Ser Leu Tyr Thr Tyr
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Leu Tyr Thr Tyr Lys Pro Arg Phe Ser Gly Val Ser Ser Asp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Ser Ser Asp Gly Arg Ser Ser Thr Pro His Asn Thr Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro His Asn Thr Lys Thr Ile Gln Val Glu Phe Gln Ser Leu Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Gln Ser Leu Pro Gly Glu Ile Ile Lys Lys Pro Val Met Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

```
Lys Pro Val Met Val Ile Gly Thr Ser Thr Ser Tyr Ser Asn Ser
1               5                   10                  15
```

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Ser Asn Ser Pro Gln Asn Asn Glu Ala Phe Leu Gln Asp Leu
1               5                   10
```

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Ala Phe Leu Gln Asp Leu Glu Leu Lys Thr Ser Arg Gly Glu Ile
1               5                   10                  15
```

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Lys Gln Thr Arg Leu Ser Ile Val Arg Pro Ser Glu Gln
1               5                   10
```

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Phe Ser Gly Val Ser Ser Asp Gly Arg Ser Ser Thr Pro His
1               5                   10
```

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Ser Asp Arg Ser Ala Asp Pro Asn Asn Gln Thr Gly Ile Ser
1               5                   10
```

<210> SEQ ID NO 39
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 39

Gln Thr Thr Glu Trp Ser Ala Ser Ser Lys Ser Ser Gly Met Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ser Lys Ser Ser Gly Met Gly Val Ser Thr Arg Val Thr Asn
1               5                   10                  15

<210> SEQ ID NO 41
<211> LENGTH: 354
<212> TYPE: PRT
<213> ORGANISM: Mus sp.

<400> SEQUENCE: 41

Met Ser Leu Phe Leu Arg Lys Arg Cys Leu Cys Leu Gly Phe Leu Leu
1               5                   10                  15

Phe His Leu Leu Ser Gln Val Ser Ala Ser Leu Arg Cys Pro Ser Arg
                20                  25                  30

Cys Pro Pro Lys Cys Pro Ser Ile Ser Pro Thr Cys Ala Pro Gly Val
            35                  40                  45

Arg Ser Val Leu Asp Gly Cys Ser Cys Cys Pro Val Cys Ala Arg Gln
        50                  55                  60

Arg Gly Glu Ser Cys Ser Glu Met Arg Pro Cys Asp Gln Ser Ser Gly
65                  70                  75                  80

Leu Tyr Cys Asp Arg Ser Ala Asp Pro Asn Asn Gln Thr Gly Ile Cys
                85                  90                  95

Met Val Pro Glu Gly Asp Asn Cys Val Phe Asp Gly Val Ile Tyr Arg
                100                 105                 110

Asn Gly Glu Lys Phe Glu Pro Asn Cys Gln Tyr Phe Cys Thr Cys Arg
            115                 120                 125

Asp Gly Gln Ile Gly Cys Leu Pro Arg Cys Gln Leu Asp Val Leu Leu
        130                 135                 140

Pro Gly Pro Asp Cys Pro Ala Pro Arg Lys Val Ala Val Pro Gly Glu
145                 150                 155                 160

Cys Cys Glu Lys Trp Thr Cys Gly Ser Asp Glu Gln Gly Thr Gln Gly
                165                 170                 175

Thr Leu Gly Gly Leu Ala Leu Pro Ala Tyr Arg Pro Glu Ala Thr Val
                180                 185                 190

Gly Val Glu Val Ser Asp Ser Ser Ile Asn Cys Ile Glu Gln Thr Thr
            195                 200                 205

Glu Trp Ser Ala Cys Ser Lys Ser Cys Gly Met Gly Val Ser Thr Arg
        210                 215                 220

Val Thr Asn Arg Asn Arg Gln Cys Glu Met Val Lys Gln Thr Arg Leu
225                 230                 235                 240

Cys Ile Val Arg Pro Cys Glu Gln Glu Pro Glu Val Thr Asp Lys
                245                 250                 255
```

-continued

Lys Gly Lys Lys Cys Leu Arg Thr Lys Ser Leu Lys Ala Ile His
            260                 265                 270

Leu Gln Phe Glu Asn Cys Thr Ser Leu Tyr Thr Tyr Lys Pro Arg Phe
        275                 280                 285

Cys Gly Val Cys Ser Asp Gly Arg Cys Cys Thr Pro His Asn Thr Lys
    290                 295                 300

Thr Ile Gln Val Glu Phe Gln Cys Leu Pro Gly Glu Ile Ile Lys Lys
305                 310                 315                 320

Pro Val Met Val Ile Gly Thr Cys Thr Cys Tyr Ser Asn Cys Pro Gln
                325                 330                 335

Asn Asn Glu Ala Phe Leu Gln Asp Leu Glu Leu Lys Thr Ser Arg Gly
            340                 345                 350

Glu Ile

<210> SEQ ID NO 42
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ser Leu Phe Leu Arg Lys Arg Ser Leu Ser Leu Gly Phe Leu Leu
1               5                   10                  15

Phe His Leu Leu Ser Gln Val Ser Ala Ser Leu Arg Ser Pro Ser Arg
            20                  25                  30

Ser Pro Pro Lys Ser Pro Ser Ile Ser Pro Thr Ser Ala Pro Gly Val
        35                  40                  45

Arg Ser Val Leu Asp Gly Ser Ser Ser Pro Val Ser Ala Arg Gln
    50                  55                  60

Arg Gly Glu Ser Ser Ser Glu Met Arg Pro Ser Asp Gln Ser Ser Gly
65                  70                  75                  80

Leu Tyr Ser Asp Arg Ser Ala Asp Pro Asn Asn Gln Thr Gly Ile Ser
                85                  90                  95

Met Val Pro Glu Gly Asp Asn Ser Val Phe Asp Gly Val Ile Tyr Arg
            100                 105                 110

Asn Gly Glu Lys Phe Glu Pro Asn Ser Gln Tyr Phe Ser Thr Ser Arg
        115                 120                 125

Asp Gly Gln Ile Gly Ser Leu Pro Arg Ser Gln Leu Asp Val Leu Leu
    130                 135                 140

Pro Gly Pro Asp Ser Pro Ala Pro Arg Lys Val Ala Val Pro Gly Glu
145                 150                 155                 160

Ser Ser Glu Lys Trp Thr Ser Gly Ser Asp Glu Gln Gly Thr Gln Gly
                165                 170                 175

Thr Leu Gly Gly Leu Ala Leu Pro Ala Tyr Arg Pro Glu Ala Thr Val
            180                 185                 190

Gly Val Glu Val Ser Asp Ser Ile Asn Ser Ile Glu Gln Thr Thr
        195                 200                 205

Glu Trp Ser Ala Ser Ser Lys Ser Ser Gly Met Gly Val Ser Thr Arg
    210                 215                 220

Val Thr Asn Arg Asn Arg Gln Ser Glu Met Val Lys Gln Thr Arg Leu
225                 230                 235                 240

Ser Ile Val Arg Pro Ser Glu Gln Glu Pro Glu Glu Val Thr Asp Lys
                245                 250                 255

```
Lys Gly Lys Lys Ser Leu Arg Thr Lys Ser Leu Lys Ala Ile His
            260                 265                 270

Leu Gln Phe Glu Asn Ser Thr Ser Leu Tyr Thr Tyr Lys Pro Arg Phe
        275                 280                 285

Ser Gly Val Ser Ser Asp Gly Arg Ser Ser Thr Pro His Asn Thr Lys
        290                 295                 300

Thr Ile Gln Val Glu Phe Gln Ser Leu Pro Gly Glu Ile Ile Lys Lys
305                 310                 315                 320

Pro Val Met Val Ile Gly Thr Ser Thr Ser Tyr Ser Asn Ser Pro Gln
                325                 330                 335

Asn Asn Glu Ala Phe Leu Gln Asp Leu Glu Leu Lys Thr Ser Arg Gly
            340                 345                 350

Glu Ile

<210> SEQ ID NO 43
<211> LENGTH: 322
<212> TYPE: PRT
<213> ORGANISM: Homo sapiens

<400> SEQUENCE: 43

Val Leu Leu Ala Leu Cys Ser Arg Pro Ala Val Gly Gln Asn Cys Ser
1               5                   10                  15

Gly Pro Cys Arg Cys Pro Asp Glu Pro Ala Pro Arg Cys Pro Ala Gly
                20                  25                  30

Val Ser Leu Val Leu Asp Gly Cys Gly Cys Cys Arg Val Cys Ala Lys
            35                  40                  45

Gln Leu Gly Glu Leu Cys Thr Glu Arg Asp Pro Cys Asp Pro His Lys
        50                  55                  60

Gly Leu Phe Cys Asp Phe Gly Ser Pro Ala Asn Arg Lys Ile Gly Val
65                  70                  75                  80

Cys Thr Ala Lys Asp Gly Ala Pro Cys Ile Phe Gly Gly Thr Val Tyr
                85                  90                  95

Arg Ser Gly Glu Ser Phe Gln Ser Ser Cys Lys Tyr Gln Cys Thr Cys
                100                 105                 110

Leu Asp Gly Ala Val Gly Cys Met Pro Leu Cys Ser Met Asp Val Arg
            115                 120                 125

Leu Pro Ser Pro Asp Cys Pro Phe Pro Arg Arg Val Lys Leu Pro Gly
        130                 135                 140

Lys Cys Cys Glu Glu Trp Val Cys Asp Glu Pro Lys Asp Gln Thr Val
145                 150                 155                 160

Val Gly Pro Ala Leu Ala Ala Tyr Arg Leu Glu Asp Thr Phe Gly Pro
                165                 170                 175

Asp Pro Thr Met Ile Arg Ala Asn Cys Leu Val Gln Thr Thr Glu Trp
            180                 185                 190

Ser Ala Cys Ser Lys Thr Cys Gly Met Gly Ile Ser Thr Arg Val Thr
        195                 200                 205

Asn Asp Asn Ala Ser Cys Arg Leu Glu Lys Gln Ser Arg Leu Cys Met
210                 215                 220

Val Arg Pro Cys Glu Ala Asp Leu Glu Glu Asn Ile Lys Lys Gly Lys
225                 230                 235                 240

Lys Cys Ile Arg Thr Pro Lys Ile Ser Lys Pro Ile Lys Phe Glu Leu
                245                 250                 255

Ser Gly Cys Thr Ser Met Lys Thr Tyr Arg Ala Lys Phe Cys Gly Val
            260                 265                 270
```

```
Cys Thr Asp Gly Arg Cys Cys Thr Pro His Arg Thr Thr Leu Pro
            275                 280                 285

Val Glu Phe Lys Cys Pro Asp Gly Glu Val Met Lys Lys Asn Met Met
    290                 295                 300

Phe Ile Lys Thr Cys Ala Cys His Tyr Asn Cys Pro Gly Asp Asn Asp
305                 310                 315                 320

Ile Phe

<210> SEQ ID NO 44
<211> LENGTH: 324
<212> TYPE: PRT
<213> ORGANISM: Homo sapiens

<400> SEQUENCE: 44

Leu Leu Leu His Leu Leu Gly Gln Val Ala Ala Thr Gln Arg Cys Pro
1               5                   10                  15

Pro Gln Cys Pro Gly Arg Cys Pro Ala Thr Pro Pro Thr Cys Ala Pro
            20                  25                  30

Gly Val Arg Ala Val Leu Asp Gly Cys Ser Cys Cys Leu Val Cys Ala
            35                  40                  45

Arg Gln Arg Gly Glu Ser Cys Ser Asp Leu Glu Pro Cys Asp Glu Ser
50                  55                  60

Ser Gly Leu Tyr Cys Asp Arg Ser Ala Asp Pro Ser Asn Gln Thr Gly
65                  70                  75                  80

Ile Cys Thr Ala Val Glu Gly Asp Asn Cys Val Phe Asp Gly Val Ile
                85                  90                  95

Tyr Arg Ser Gly Glu Lys Phe Gln Pro Ser Cys Lys Phe Gln Cys Thr
            100                 105                 110

Cys Arg Asp Gly Gln Ile Gly Cys Val Pro Arg Cys Gln Leu Asp Val
            115                 120                 125

Leu Leu Pro Glu Pro Asn Cys Pro Ala Pro Arg Lys Val Glu Val Pro
130                 135                 140

Gly Glu Cys Cys Glu Lys Trp Ile Cys Gly Pro Asp Glu Glu Asp Ser
145                 150                 155                 160

Leu Gly Gly Leu Thr Leu Ala Ala Tyr Arg Pro Glu Ala Thr Leu Gly
                165                 170                 175

Val Glu Val Ser Asp Ser Ser Val Asn Cys Ile Glu Gln Thr Thr Glu
            180                 185                 190

Trp Thr Ala Cys Ser Lys Ser Cys Gly Met Gly Phe Ser Thr Arg Val
            195                 200                 205

Thr Asn Arg Asn Arg Gln Cys Glu Met Leu Lys Gln Thr Arg Leu Cys
210                 215                 220

Met Val Arg Pro Cys Glu Gln Glu Pro Glu Gln Pro Thr Asp Lys Lys
225                 230                 235                 240

Gly Lys Lys Cys Leu Arg Thr Lys Lys Ser Leu Lys Ala Ile His Leu
                245                 250                 255

Gln Phe Lys Asn Cys Thr Ser Leu His Thr Tyr Lys Pro Arg Phe Cys
            260                 265                 270

Gly Val Cys Ser Asp Gly Arg Cys Cys Thr Pro His Asn Thr Lys Thr
            275                 280                 285

Ile Gln Ala Glu Phe Gln Cys Ser Pro Gly Gln Ile Val Lys Lys Pro
290                 295                 300

Val Met Val Ile Gly Thr Cys Thr Cys His Thr Asn Cys Pro Lys Asn
305                 310                 315                 320
```

Asn Glu Ala Phe

<210> SEQ ID NO 45
<211> LENGTH: 14
<212> TYPE: PRT
<213> ORGANISM: Mus sp.

<400> SEQUENCE: 45

Gln Thr Thr Glu Trp Ser Ala Cys Ser Lys Ser Cys Gly Met
1               5                   10

<210> SEQ ID NO 46
<211> LENGTH: 15
<212> TYPE: PRT
<213> ORGANISM: Mus sp.

<400> SEQUENCE: 46

Cys Ser Lys Ser Cys Gly Met Gly Val Ser Thr Arg Val Thr Asn
1               5                   10                  15

<210> SEQ ID NO 47
<211> LENGTH: 13
<212> TYPE: PRT
<213> ORGANISM: Mus sp.

<400> SEQUENCE: 47

Lys Gln Thr Arg Leu Cys Ile Val Arg Pro Cys Glu Gln
1               5                   10

<210> SEQ ID NO 48
<211> LENGTH: 14
<212> TYPE: PRT
<213> ORGANISM: Mus sp.

<400> SEQUENCE: 48

Phe Cys Gly Val Cys Ser Asp Gly Arg Cys Cys Thr Pro His
1               5                   10

<210> SEQ ID NO 49
<211> LENGTH: 14
<212> TYPE: PRT
<213> ORGANISM: Mus sp.

<400> SEQUENCE: 49

Cys Asp Arg Ser Ala Asp Pro Asn Asn Gln Thr Gly Ile Cys
1               5                   10

<210> SEQ ID NO 50
<211> LENGTH: 14
<212> TYPE: PRT
<213> ORGANISM: Homo sapiens

<400> SEQUENCE: 50

Cys Asp Arg Ser Ala Asp Pro Ser Asn Gln Thr Gly Ile Cys
1               5                   10

<210> SEQ ID NO 51
<211> LENGTH: 14
<212> TYPE: PRT
<213> ORGANISM: Homo sapiens

<400> SEQUENCE: 51

Phe Cys Gly Val Cys Thr Asp Gly Arg Cys Cys Thr Pro His
1               5                   10

<210> SEQ ID NO 52
<211> LENGTH: 14
<212> TYPE: PRT
<213> ORGANISM: Rattus sp.

<400> SEQUENCE: 52

Cys Asp Arg Ser Ala Asp Pro Asn Asn Glu Thr Gly Ile Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Asp Arg Ser Ala Asp Pro Asn Asn Glu Thr Gly Ile Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Val Ser Ser Asp Gly Arg Ser Ser Thr Pro His
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Ser Gly Val Ser Ser Asp Gly Arg Ser Ser Thr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Asp Arg Ser Ala Asp Pro Ser Asn Gln Thr Gly Ile Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Ala Asp Pro Ser Asn Gln Thr Gly Ile Ser

-continued

```
<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Asp Arg Ser Ala Asp Pro Ser Asn Gln Thr Gly Ile Ser Thr
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Ala Asp Pro Asn Asn Gln Thr Gly Ile Ser
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ser Ala Asp Pro Asn Asn Glu Thr Gly Ile Ser
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Asp Arg Ser Ala Asp Pro Ser Asn Glu Thr Gly Ile Ser Thr
1               5                   10                  15

<210> SEQ ID NO 62
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Leu Leu His Leu Leu Gly Gln Val Ala Ala Thr Gln Arg Ser Pro
1               5                   10                  15

Pro Gln Ser Pro Gly Arg Ser Pro Ala Thr Pro Thr Ser Ala Pro
            20                  25                  30

Gly Val Arg Ala Val Leu Asp Gly Ser Ser Ser Leu Val Ser Ala
        35                  40                  45

Arg Gln Arg Gly Glu Ser Ser Ser Asp Leu Glu Pro Ser Asp Glu Ser
```

```
            50                  55                  60
Ser Gly Leu Tyr Ser Asp Arg Ser Ala Asp Pro Ser Asn Gln Thr Gly
 65                  70                  75                  80

Ile Ser Thr Ala Val Glu Gly Asp Asn Ser Val Phe Asp Gly Val Ile
                 85                  90                  95

Tyr Arg Ser Gly Glu Lys Phe Gln Pro Ser Ser Lys Phe Gln Ser Thr
                100                 105                 110

Ser Arg Asp Gly Gln Ile Gly Ser Val Pro Arg Ser Gln Leu Asp Val
                115                 120                 125

Leu Leu Pro Glu Pro Asn Ser Pro Ala Pro Arg Lys Val Glu Val Pro
            130                 135                 140

Gly Glu Ser Ser Glu Lys Trp Ile Ser Gly Pro Asp Glu Glu Asp Ser
145                 150                 155                 160

Leu Gly Gly Leu Thr Leu Ala Ala Tyr Arg Pro Glu Ala Thr Leu Gly
                165                 170                 175

Val Glu Val Ser Asp Ser Ser Val Asn Ser Ile Glu Gln Thr Thr Glu
                180                 185                 190

Trp Thr Ala Ser Ser Lys Ser Ser Gly Met Gly Phe Ser Thr Arg Val
                195                 200                 205

Thr Asn Arg Asn Arg Gln Ser Glu Met Leu Lys Gln Thr Arg Leu Ser
            210                 215                 220

Met Val Arg Pro Ser Glu Gln Glu Pro Glu Gln Pro Thr Asp Lys Lys
225                 230                 235                 240

Gly Lys Lys Ser Leu Arg Thr Lys Lys Ser Leu Lys Ala Ile His Leu
                245                 250                 255

Gln Phe Lys Asn Ser Thr Ser Leu His Thr Tyr Lys Pro Arg Phe Ser
                260                 265                 270

Gly Val Ser Ser Asp Gly Arg Ser Ser Thr Pro His Asn Thr Lys Thr
                275                 280                 285

Ile Gln Ala Glu Phe Gln Ser Ser Pro Gly Gln Ile Val Lys Lys Pro
            290                 295                 300

Val Met Val Ile Gly Thr Ser Thr Ser His Thr Asn Ser Pro Lys Asn
305                 310                 315                 320

Asn Glu Ala Phe

<210> SEQ ID NO 63
<211> LENGTH: 14
<212> TYPE: PRT
<213> ORGANISM: Homo sapiens

<400> SEQUENCE: 63

Phe Cys Gly Val Cys Ser Asp Gly Arg Cys Cys Thr Pro His
1               5                   10

<210> SEQ ID NO 64
<211> LENGTH: 14
<212> TYPE: PRT
<213> ORGANISM: Homo sapiens

<400> SEQUENCE: 64

Cys Asp Phe Gly Ser Pro Ala Asn Arg Lys Ile Gly Val Cys
1               5                   10

<210> SEQ ID NO 65
<211> LENGTH: 14
<212> TYPE: PRT
<213> ORGANISM: Mus sp.
```

<400> SEQUENCE: 65

Phe Cys Gly Val Cys Thr Asp Gly Arg Cys Cys Thr Pro His
1               5                   10

<210> SEQ ID NO 66
<211> LENGTH: 14
<212> TYPE: PRT
<213> ORGANISM: Mus sp.

<400> SEQUENCE: 66

Cys Asp Phe Gly Ser Pro Ala Asn Arg Lys Ile Gly Val Cys
1               5                   10

<210> SEQ ID NO 67
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Gln Val Ala Ala Thr Gln Arg Cys Pro Pro Gln Cys Pro Gly Arg
1               5                   10                  15

Cys Pro Ala Thr Pro Pro Thr Cys Ala Pro Gly Val Arg Ala Val Leu
                20                  25                  30

Asp Gly Cys Ser Cys Cys Leu Val Cys Ala Arg Gln Arg Gly Glu Ser
            35                  40                  45

Cys Ser Asp Leu Glu Pro Cys Asp Glu Ser Ser Gly Leu Tyr Cys Asp
    50                  55                  60

Arg Ser Ala Asp Pro Ser Asn Gln Thr Gly Ile Cys Thr Ala Val Glu
65                  70                  75                  80

Gly Asp Asn Cys Val Phe Asp Gly Val Ile Tyr Arg Ser Gly Glu Lys
                85                  90                  95

Phe Gln Pro Ser Cys Lys Phe Gln Cys Thr Cys Arg Asp Gly Gln Ile
                100                 105                 110

Gly Cys Val Pro Arg Cys Gln Leu Asp Val Leu Leu Pro Glu Pro Asn
            115                 120                 125

Cys Pro Ala Pro Arg Lys Val Glu Val Pro Gly Glu Cys Cys Glu Lys
    130                 135                 140

Trp Ile Cys Gly Pro Asp Glu Glu Asp Ser Leu Gly Gly Leu Thr Leu
145                 150                 155                 160

Ala Ala Tyr Arg Pro Glu Ala Thr Leu Gly Val Glu Val Ser Asp Ser
                165                 170                 175

Ser Val Asn Cys Ile Glu Gln Thr Thr Glu Trp Thr Ala Cys Ser Lys
            180                 185                 190

Ser Cys Gly Met Gly Phe Ser Thr Arg Val Thr Asn Arg Asn Arg Gln
        195                 200                 205

Cys Glu Met Leu Lys Gln Thr Arg Leu Cys Met Val Arg Pro Cys Glu
    210                 215                 220

Gln Glu Pro Glu Gln Pro Thr Asp Lys Lys Gly Lys Lys Cys Leu Arg
225                 230                 235                 240

Thr Lys Lys Ser Leu Lys Ala Ile His Leu Gln Phe Lys Asn Cys Thr
                245                 250                 255

Ser Leu His Thr Tyr Lys Pro Arg Phe Cys Gly Val Cys Ser Asp Gly
            260                 265                 270

-continued

```
Arg Cys Cys Thr Pro His Asn Thr Lys Thr Ile Gln Ala Glu Phe Gln
        275                 280                 285

Cys Ser Pro Gly Gln Ile Val Lys Lys Pro Val Met Val Ile Gly Thr
    290                 295                 300

Cys Thr Cys His Thr Asn Cys Pro Lys Asn Asn Glu Ala Phe Leu Gln
305                 310                 315                 320

Glu Leu Glu Leu Lys Thr Thr Arg Gly Lys Met
                325                 330
```